(12) United States Patent
Quan et al.

(10) Patent No.: US 9,592,402 B2
(45) Date of Patent: Mar. 14, 2017

(54) SHOCK DETERMINATION BASED ON PRIOR SHOCKS

(71) Applicant: ZOLL Medical Corporation, Chelmsford, MA (US)

(72) Inventors: Weilun Quan, Dracut, MA (US); Gary A. Freeman, Newton Center, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 14/211,321

(22) Filed: Mar. 14, 2014

(65) Prior Publication Data

US 2014/0277224 A1  Sep. 18, 2014

Related U.S. Application Data

(60) Provisional application No. 61/784,139, filed on Mar. 14, 2013.

(51) Int. Cl.
*A61N 1/39* (2006.01)
*H01L 23/532* (2006.01)

(52) U.S. Cl.
CPC ......... *A61N 1/3931* (2013.01); *A61N 1/3987* (2013.01); *H01L 23/53238* (2013.01); *H01L 23/53257* (2013.01); *H01L 2924/0002* (2013.01)

(58) Field of Classification Search
CPC ............... A61N 1/3987; A61N 1/3625; A61N 1/36014; A61N 1/3627
USPC ....................................................... 607/6, 7
See application file for complete search history.

(56) References Cited

U.S. PATENT DOCUMENTS

| | | | |
|---|---|---|---|
| 5,077,667 A | 12/1991 | Brown et al. |
| 5,092,341 A | 3/1992 | Kelen |
| 5,741,304 A | 4/1998 | Patwardhan et al. |
| 5,957,856 A | 9/1999 | Weil et al. |
| 6,171,257 B1 | 1/2001 | Weil et al. |
| 6,224,562 B1 | 5/2001 | Lurie et al. |

(Continued)

FOREIGN PATENT DOCUMENTS

| | | |
|---|---|---|
| WO | 2011/100534 | 8/2011 |
| WO | WO 2012/059846 | 5/2012 |

(Continued)

OTHER PUBLICATIONS

Chaudhry, Fahd A., A Novel Resuscitation Algorithm Using Waveform Analysis and End-Tidal Carbon Dioxide Pressure for Ventricular Fibrillation, University of Arizona, Biomedical Engineering Interdisciplinary Program, 2011, 39 pages.

(Continued)

*Primary Examiner* — Alyssa M Alter
(74) *Attorney, Agent, or Firm* — Fish & Richardson P.C.

(57) ABSTRACT

A system for managing care of a person receiving emergency cardiac assistance is disclosed that includes one or more capacitors for delivering a defibrillating shock to a patient; one or more electronic ports for receiving signals from sensors for obtaining indications of an electrocardiogram (ECG) for the patient; a patient treatment module executable on one or more computer processors to provide a determination of a likelihood of success from delivering a future defibrillating shock to the person with the one or more capacitors, using (a) information about a prior defibrillating shock, and (b) a value that is a function of current ECG signals from the patient.

33 Claims, 13 Drawing Sheets

(56) References Cited

U.S. PATENT DOCUMENTS

| | | | |
|---|---|---|---|
| 6,694,187 B1* | 2/2004 | Freeman | A61N 1/39 607/5 |
| 6,760,621 B2 | 7/2004 | Walcott | |
| 6,813,517 B2 | 11/2004 | Daynes et al. | |
| 7,269,454 B2 | 9/2007 | Sherman | |
| 7,593,772 B2 | 9/2009 | Sherman | |
| 7,774,060 B2 | 8/2010 | Westenskow | |
| 7,813,791 B1 | 10/2010 | Gill | |
| 7,831,299 B2 | 11/2010 | Tan et al. | |
| 7,920,917 B2 | 4/2011 | Kelly | |
| 8,165,671 B2 | 4/2012 | Freeman et al. | |
| 8,868,179 B2 | 10/2014 | Quan et al. | |
| 8,948,859 B2 | 2/2015 | Freeman et al. | |
| 9,180,304 B2 | 11/2015 | Quan et al. | |
| 9,186,521 B2 | 11/2015 | Quan et al. | |
| 2002/0026229 A1 | 2/2002 | Weil et al. | |
| 2002/0133197 A1 | 9/2002 | Snyder et al. | |
| 2002/0138106 A1 | 9/2002 | Christini et al. | |
| 2003/0055460 A1 | 3/2003 | Owen et al. | |
| 2004/0039419 A1 | 2/2004 | Stickney et al. | |
| 2004/0116969 A1 | 6/2004 | Owen | |
| 2004/0215271 A1* | 10/2004 | Sullivan | A61B 5/0408 607/27 |
| 2005/0080828 A1 | 4/2005 | Johnson | |
| 2005/0245974 A1 | 11/2005 | Sherman | |
| 2005/0267536 A1 | 12/2005 | Freeman et al. | |
| 2006/0025824 A1 | 2/2006 | Freeman | |
| 2006/0116724 A1 | 6/2006 | Snyder | |
| 2007/0060785 A1 | 3/2007 | Freeman et al. | |
| 2007/0100381 A1 | 5/2007 | Snyder et al. | |
| 2008/0145827 A1 | 6/2008 | Strand et al. | |
| 2008/0208070 A1 | 8/2008 | Snyder et al. | |
| 2009/0270930 A1 | 10/2009 | Walker | |
| 2010/0268059 A1 | 10/2010 | Ryu et al. | |
| 2011/0021938 A1 | 1/2011 | Anderson et al. | |
| 2011/0034816 A1 | 2/2011 | Tan et al. | |
| 2011/0202100 A1* | 8/2011 | Tan | A61H 31/005 607/6 |
| 2011/0202101 A1 | 8/2011 | Tan | |
| 2011/0295127 A1 | 12/2011 | Sandler et al. | |
| 2012/0010543 A1 | 1/2012 | Johnson et al. | |
| 2012/0226178 A1 | 9/2012 | Freeman et al. | |
| 2013/0138168 A1 | 5/2013 | Quan et al. | |
| 2013/0144181 A1 | 6/2013 | Fogt et al. | |
| 2013/0190634 A1 | 7/2013 | Phillips | |
| 2013/0218057 A1 | 8/2013 | Jorgenson | |
| 2014/0236030 A1 | 8/2014 | Tan et al. | |
| 2014/0277228 A1 | 9/2014 | Quan et al. | |
| 2015/0257709 A1 | 9/2015 | Quan et al. | |
| 2015/0257715 A1 | 9/2015 | Quan et al. | |
| 2015/0352367 A1 | 12/2015 | Quan et al. | |
| 2015/0352369 A1 | 12/2015 | Quan et al. | |
| 2016/0023010 A1 | 1/2016 | Quan et al. | |
| 2016/0082278 A1 | 3/2016 | Quan et al. | |

FOREIGN PATENT DOCUMENTS

| | | |
|---|---|---|
| WO | WO 2012/072518 | 6/2012 |
| WO | 2013/071280 | 5/2013 |

OTHER PUBLICATIONS

International Search Report and Written Opinion, PCT/US2014/027431, mailed Aug. 11, 2014, 14 pages.

International Search Report and Written Opinion, PCT/US2014/27514, mailed Aug. 11, 2014, 14 pages.

International Search Report and Written Opinion, PCT/US2014/27658, mailed Aug. 25, 2014, 19 pages.

Lee, Seungyup, "Mapping the Characteristics of Atrial Activation Patterns During Atrial Fibrillation," Case Western Reserve University: Department of Biomedical Engineering, Jan. 2013, 34 pages.

Chinese Office Action, CN Application 201480027256.X, issued May 30, 2016, 8 pages.

Extended European Search Report, PCT/US2012/065779, Aug. 14, 2015, 7 pages.

Extended European Search Report, European Patent Application No. 13804051.4, dated Feb. 4, 2016, 9 pages.

International Search Report and Written Opinion, PCT/US2012/64779, Feb. 1, 2013, 8 pages.

International Search Report and Written Opinion, PCT/US2015/35174, mailed Sep. 17, 2015, 13 pages.

International Search Report and Written Opinion, PCT/US2015/35189, mailed Nov. 3, 2015, 20 pages.

International Search Report and Written Opinion from corresponding PCT/US2013/44750 mailed Sep. 20, 2013.

Povoas et al., "Predicting the success of defibrillation by electrocardiographic analysis," Resuscitation 53(1):77-82 (2002).

Watson et al., "Rapid Communication; Wavelet transform-based prediction of the likelihood of successful defibrillation for patients exhibiting ventricular fibrillation; Rapid Communication", Measurement Science and Technology, IOP, Bristol, GB, vol. 16, No. 10, Oct. 1, 2005, pp. L1-L6.

Compos et al., "An Up-Down Bayesian, Defibrillation Efficacy Estimator", PACE—Pacing and Clinical Electrophysiology, Blackwell Futura Publishing, Malden, MA, US, vol. 20, No. 5, Part 01, May 1, 1997, pp. 1292-1300.

European Search Report, 14768658.8, Feb. 12, 2016, 10 pages.

Huang et al, "Quantification of activation patterns during ventricular fibrillation in open-chest porcine left ventricle and septum", Heart Rhythm Elsevier, US, vol. 2, No. 7, Jul. 1, 2005, pp. 720-728.

* cited by examiner

| | 1st vs 2nd DF | 2nd vs 3rd DF | 3rd vs 4th DF | 4th vs 5th DF |
|---|---|---|---|---|
| AMSA changes between DFs | 12.24+0.62 vs. 9.94+0.48* | 8.60+0.34 vs. 9.41+0.58# | 9.47+0.91 vs. 8.58+0.62# | # |

| Selected AMSA thresholds | Events of correct prediction of 'non successful' DF | overall |
|---|---|---|
| First DF (n=609) | | |
| 5 | 101 (N=102) | 99 |
| 5.5 | 124 (N=126) | 98.4 |
| 6 | 147 (N=153) | 96.1 |
| 6.5 | 175 (N=184) | 95.1 |
| 7 | 198 (N=213) | 93 |
| 7.5 | 213 (N=229) | 93 |
| Subsequent DFs (n=662) | | |
| 5 | 165 (N=168) | 98.2 |
| 5.5 | 205 (N=210) | 97.6 |
| 6 | 245 (N=254) | 96.5 |
| 6.5 | 272 (N=283) | 96.1 |
| 7 | 301 (N=317) | 95 |
| 7.5 | 328 (N=346) | 95 |

DF, defibrillation; *p<0.0001, #p>0.1

FIG. 1C

| 0 Shocks | 1 Shock | 2 Shocks | 3 Shocks | |
|---|---|---|---|---|
| 100 | 90 | 80 | 70 | 90% |
| 90 | 80 | 70 | 60 | 80% |
| 80 | 70 | 60 | 50 | 70% |
| 70 | 60 | 50 | 40 | 60% |
| 60 | 50 | 40 | 30 | 50% |

FIG. 1D

| AMSA mV-Hz | Sensitivity % | Specificity % | PPV % | NPV % | % |
|---|---|---|---|---|---|
| 1 | 100 | 1 | 27 | 100 | 28 |
| 2 | 100 | 5 | 28 | 100 | 31 |
| 3 | 100 | 11 | 29 | 100 | 35 |
| 4 | 99 | 18 | 31 | 99 | 40 |
| 5 | 99 | 27 | 34 | 99 | 47 |
| 6 | 99 | 40 | 38 | 99 | 56 |
| 7 | 96 | 49 | 41 | 97 | 62 |
| 8 | 87 | 59 | 44 | 93 | 67 |
| 9 | 83 | 65 | 47 | 91 | 70 |
| 10 | 73 | 72 | 49 | 88 | 72 |
| 11 | 67 | 76 | 51 | 86 | 74 |
| 12 | 60 | 80 | 53 | 84 | 75 |
| 13 | 53 | 82 | 52 | 83 | 74 |
| 14 | 48 | 84 | 53 | 81 | 75 |
| 15 | 42 | 87 | 54 | 80 | 75 |
| 16 | 37 | 91 | 59 | 79 | 76 |
| 17 | 31 | 92 | 60 | 78 | 76 |
| 18 | 23 | 93 | 54 | 77 | 74 |
| 19 | 21 | 94 | 55 | 76 | 74 |
| 20 | 21 | 95 | 58 | 76 | 75 |
| 25 | 10 | 97 | 53 | 74 | 73 |
| 30 | 3 | 99 | 50 | 73 | 73 |
| 40 | 2 | 100 | 78 | 74 | 74 |
| 50 | 1 | 100 | 100 | 74 | 74 |

FIG. 1E

|  | Refractory VF (n=543) | Recurrent VF (n=139) |
|---|---|---|
| Mean AMSA, mV-Hz | 7.6 ± 0.2 | 16.2 ± 0.9* |
| AMSA prior to successful DFs, mV-Hz | 12.7 ± 1 | 16.8 ± 1 |
| AMSA prior to failing DFs, mV-Hz | 7 ± 0.2 # | 13.8 ± 1.8 |
| Successful DFs, % (n) | 9.2 (50/543) | 79.1 (110/139) |

DFs, defibrillation attempts; VF, ventricular fibrillation; Mean ± SEM;
* $p < 0.0001$ vs. refractory VF; # $p < 0.0001$ vs. successful DFs

FIG. 1F

| AMSA mV-Hz | Sensitivity % | Specificity % | PPV % | NPV % | Accuracy % |
|---|---|---|---|---|---|
| 1 | 98 | 0 | 9 | 50 | 9 |
| 2 | 96 | 1 | 9 | 75 | 10 |
| 3 | 96 | 3 | 9 | 89 | 12 |
| 4 | 94 | 11 | 10 | 95 | 19 |
| 5 | 94 | 32 | 12 | 98 | 38 |
| 6 | 90 | 49 | 15 | 98 | 53 |
| 7 | 86 | 63 | 19 | 98 | 65 |
| 8 | 82 | 72 | 23 | 98 | 73 |
| 9 | 68 | 80 | 25 | 96 | 79 |
| 10 | 58 | 86 | 30 | 95 | 84 |
| 11 | 50 | 90 | 34 | 95 | 87 |
| 12 | 42 | 92 | 34 | 94 | 87 |
| 13 | 34 | 94 | 36 | 93 | 88 |
| 14 | 32 | 96 | 42 | 93 | 90 |
| 15 | 30 | 96 | 45 | 93 | 90 |
| 16 | 28 | 97 | 49 | 93 | 91 |
| 17 | 26 | 97 | 50 | 93 | 91 |
| 18 | 22 | 98 | 50 | 93 | 91 |
| 19 | 16 | 98 | 50 | 92 | 91 |
| 20 | 10 | 98 | 39 | 92 | 90 |
| 25 | 4 | 100 | 50 | 91 | 91 |
| 30 | 2 | 100 | 33 | 91 | 91 |
| 40 | 0 | 100 | 100 | 91 | 91 |

FIG. 1G

SHOCK DETERMINATION BASED ON PRIOR SHOCKS

CLAIM OF PRIORITY

This application claims priority under 35 USC §119(e) to U.S. Patent Application Ser. No. 61/784,139, filed on Mar. 14, 2013, the entire contents of which are hereby incorporated by reference.

TECHNICAL FIELD

This document relates to cardiac resuscitation, and in particular to systems and techniques for determining when a defibrillating shock on a person will be effective.

BACKGROUND

Heart attacks are a common cause of death. A heart attack occurs when a portion of the heart tissue loses circulation and becomes damaged as a result (e.g., because of blockage in the heart vasculature). Heart attacks and other abnormalities can lead to ventricular fibrillation (VF), which is an abnormal heart rhythm (arrhythmia) that causes the heart to lose pumping capacity. If such a problem is not corrected quickly—typically within minutes—the rest of the body loses oxygen and the person dies. Therefore, prompt care of a person undergoing ventricular fibrillation can be key to a positive outcome for such a person.

One common way to treat ventricular fibrillation is through the use of an electrical defibrillator that delivers a relatively high voltage shock to the heart in order to force it back to a normal, consistent, and strong rhythm. People who have had previous problems with ventricular fibrillation may be implanted with an automatic defibrillator that constantly monitors the condition of their heart and applies a shock when necessary. Other such people may be provided with a wearable defibrillator in the form of a vest such as the LIFEVEST product from ZOLL Medical Corporation. Other people may be treated using an external defibrillator, such as in a hospital or via an automatic external defibrillator (AED) of the kind that is frequently seen in airports, public gymnasiums, and other public spaces.

People undergoing ventricular fibrillation may be more receptive to a defibrillating shock in some instances compared to others. For example, research has determined that a computation of amplitude spectrum area (AMSA), or other computational methods that use either time-based or spectrum-based analytic methods to calculate from an electrocardiogram (ECG) a prediction of defibrillation shock success, may indicate whether a shock that is delivered to a person will likely result in successful defibrillation or will instead likely fail.

SUMMARY

This document describes systems and techniques that may be used to help determine when a shock on a person suffering from VF will likely be successful, i.e., will defibrillate the person. Such a determination may then be used to guide someone (e.g., a physician, EMT, or lay rescuer) performing rescue operations on that person (also referred to here as a patient or victim), such as by a portable defibrillator providing an indication, on a graphical display of the defibrillator or another device or audibly, that a shock should or should not be provided. In implementations described below, for example, such systems and techniques may take into account the success or lack of success in prior attempts to defibrillate the person (where there has been recurrent or refractory VF—where recurrent VF results after a successful prior defibrillating shock and refractory VF results after an unsuccessful prior defibrillating shock), among other factors, such as a current AMSA value for the person and trans-thoracic impedance level of the person.

As one example, a threshold AMSA value may be set, at which level the shocking ability of a defibrillator is made available to a rescuer, or at which a likelihood of success that is displayed to the rescuer may change (e.g., AMSA values between X and Y may show a likelihood of m percent, while AMSA values between Y and Z may show a likelihood value of n percent) based on whether prior successful defibrillating shocks that have been given to a patient have been successful. For example, the relevant AMSA threshold for generating a certain output or action of a defibrillator (such as the display to the user just mentioned) may be adjusted based on determinations about the success of prior shocks and on the trans-thoracic impedance. Thus, for example, an AMSA value or values may be computed from incoming ECG signals from the person, and decisions may be made by comparing the computed AMSA value to stored thresholds, where the thresholds may change based on the other factors or the AMSA value may be adjusted using the other factors and then be compared to thresholds that do not change. Generally, there is no practical difference between changing the value and making static the thresholds against which it is compared versus changing the thresholds and leaving the value set.

Such adjustments, when based on determinations about the success or lack of success of prior defibrillation efforts, may be made in a variety of ways. For example, AMSA threshold values (which are reduced for recurrent VF) associated with future successful defibrillation have been determined to fall substantially when there has been a prior successful defibrillation during an emergency with a particular patient. (Unless indicated otherwise, all values that are collected, computed, and compared here are for a single adverse cardiac event for a patient.) Such correlations may be determined by analysis of historical defibrillation activity (e.g., collected by portable defibrillators deployed in the field for actual cardiac events), and may be used to produce a mapping between observed past likelihood of success for various AMSA values and levels of prior successful defibrillations. Such data may be used, for example, to generate a look-up table or similar structure that can be loaded on other deployed (e.g., via network and/or wireless data updates) or to-be-deployed defibrillators, which can be consulted in the future during other cardiac events. For example, the number of prior successful defibrillations for an event may be along one axis of a table, and an AMSA score may be along another, and those other defibrillators may employ both values for a victim, with the table producing an indication of a likelihood of a to-be-applied shock being successful. The table or other data structure may also have additional dimensions, such as a dimension that identifies trans-thoracic impedance, and dimensions that identify other variables whose values that have been determined to be relevant to whether an applied shock will likely be successful.

Upon making such a determination of a likelihood of future success, a defibrillator may provide an indication to a rescuer about such a determination. For example, the defibrillator may only allow a shock to be performed when the indication is sufficiently positive (e.g., over a set percentage of likelihood of success). Also, a defibrillator may provide a display—such as a graphic that shows whether defibrillation will likely succeed (e.g., above a predetermine threshold level of likelihood of success) or providing a number (e.g., a percentage of likelihood of success) or other indication (e.g., a grade of A, B, C, D, or F) so that the rescuer can determine whether to apply a shock.

The device can also change the indication it presents in different situations, e.g., a dual-mode defibrillator could simply indicate whether defibrillation is advised (and may refuse to permit delivery of a shock when it is not advised) when the defibrillator is in AED mode, and may provide more nuanced information when the defibrillator is in manual mode, and thus presumably being operated by someone who can better interpret such information and act properly on it.

In certain implementations, such systems and techniques may provide one or more advantages. For example, a determination of whether a shock should be provided can be made from values that are already being measured for a patient (e.g., trans-thoracic impedance may already be used by a defibrillator to affect the shape of the voltage of the waveform that is provided to the patient). For example, the determination may be improved compared to simply measuring AMSA, and may thus result in better performance for a system and better outcomes for a patient. In particular, a defibrillator may cause a rescuer to wait to provide a defibrillating shock until a time at which the shock is more likely to be effective. As a result, the patient may avoid receiving an ineffective shock, and then having to wait another cycle for another shock (which may end up being equally ineffective). Such a process may, therefore, result in the patient returning to normal cardiac function more quickly and with less stress on his or her cardiac system, which will generally lead to better patient outcomes.

In one implementation, a system for managing care of a person receiving emergency cardiac assistance is disclosed. The system comprises one or more capacitors for delivering a defibrillating shock to a patient; one or more electronic ports for receiving signals from sensors for obtaining indications of an electrocardiogram (ECG) for the patient; and a patient treatment module executable on one or more computer processors to provide a determination of a likelihood of success from delivering a future defibrillating shock to the person with the one or more capacitors, using (a) information about a prior defibrillating shock, and (b) a value that is a function of current ECG signals from the patient. The system can also include an output mechanism arranged to indicate, to a user of the system, an indication regarding the likelihood of success form delivering a defibrillating shock to the person with the one or more capacitors. The output mechanism can include a visual display, and the system can be programmed to display to the user one of multiple possible indications that each indicate a degree of likelihood of success. Alternatively or in addition, the output mechanism can comprise an interlock that prevents a user from delivering a shock unless the determined likelihood of success exceeds a determined value.

In some aspects, the patient treatment module comprises an ECG analyzer for generating an amplitude spectrum area (AMSA) value, wherein the patient treatment module uses the information about the level of success from the prior defibrillating shock to adjust the AMSA value. Moreover, the patient treatment module can comprise an ECG analyzer for generating indications of heart rate for the patent, heart rate variability for the patent, ECG amplitude for the patent, and/or first or second derivatives of ECG amplitude for the patent. The indication of ECG amplitude can comprise, for example, an RMS measurement, measure peak-to-peak, peak-to-trough, or an average of peak-to-peak or peak-to-trough over a specified interval In other aspects, the patient treatment module is programmed to determine whether a prior defibrillation shock was at least partially successful, and based at least in part on the determination of whether the prior defibrillation was at least partially successful, modify a calculation of the likelihood of success from delivering the future defibrillating shock. Moreover, determining a likelihood of success from delivering a future defibrillating shock to the person can depend on a determination of whether one or more prior shocks delivered to the person were successful in defibrillating the person. In addition, determining a likelihood of success from delivering a future defibrillating shock can comprise performing a mathematical transform on the ECG data. The mathematical transform can be selected form a group consisting of Fourier, discrete Fourier, Hilbert, discrete Hilbert, wavelet, and discrete wavelet methods. In addition, determining a likelihood of success from delivering a future defibrillating shock comprises performing a calculation by an operation selected form a group consisting of logistic regression, table look-up, neural network, and fuzzy logic.

In yet another example, the patient treatment module is programmed to determine the likelihood of success from delivering a future defibrillating shock using at least one patient-dependent physical parameter separate from a patient ECG reading. The patient treatment module can also be programmed to determine the likelihood of success from delivering a future defibrillating shock using at a measure of trans-thoracic impedance of the person.

In another implementations, a method for managing care of a person receiving emergency cardiac assistance is disclosed, and comprises monitoring, with an external defibrillator, electrocardiogram (ECG) data from a person receiving emergency cardiac assistance; determining whether a prior defibrillation shock occurred; determining a likelihood of future defibrillation shock success using at least the ECG data; based at least in part on the determination of whether the prior defibrillation occurred, modifying the calculation of the chance of defibrillation shock success; and affecting control of the external defibrillator based on the identification of whether a present defibrillation shock will likely be effective. Determining a likelihood of future defibrillation shock success can comprise determining a value that is a function of electrocardiogram amplitude at particular different frequencies or frequency ranges. Determining a likelihood of future defibrillation shock success can comprise determining an amplitude spectrum area (AMSA) value for the ECG data, and can also comprise adjusting the determined AMSA value using information about the prior defibrillation shock. In addition, the method can comprise determining whether the adjusted AMSA value exceeds a predetermined threshold value.

In certain aspects, the method comprises providing to the rescuer a visual, audible, or tactile alert that a shockable situation exists for the person, if the adjusted AMSA value is determined to exceed the predetermined threshold value. The method can also include determining whether a prior defibrillation shock was at least partially successful, and based at least in part on the determination of whether the prior defibrillation was at least partially successful, modifying a calculation of the likelihood of success from delivering the future defibrillating shock. The determining of a likelihood of success from delivering a future defibrillating shock can comprise performing a mathematical transform on the ECG data, and the mathematical transform may be selected form a group consisting of Fourier, discrete Fourier, Hilbert, wavelet, and discrete wavelet methods. Also, determining a likelihood of success from delivering a future defibrillating shock can comprise performing a calculation by an operation selected form a group consisting of logistic regression, table look-up, neural network, and fuzzy logic. Moreover, the likelihood of success from delivering a future defibrillating shock can be determined using at least one patient-dependent physical parameter separate from a patient ECG reading.

In certain other aspects, the additional physiologic parameter is trans-thoracic impedance of the person receiving emergency cardiac care, and the indication of trans-thoracic impedance can be determined from signals sensed by a plurality of electrocardiogram leads that also provide the EGO data. The method may also include cyclically repeating the actions of monitoring, determining, identifying and providing the indication. The method also can comprise identifying compression depth of chest compressions performed on the person, using a device on the person's sternum and in communication with the external defibrillator, and providing feedback to a rescuer performing the chest compressions regarding rate of compression, depth of compression, or both.

Other features and advantages will be apparent from the description and drawings, and from the claims.

DESCRIPTION OF DRAWINGS

FIG. 1C is a table showing examples relating AMSA to predicted likelihood of failure in defibrillating a victim who has or has not been previously defibrillated.

FIG. 1D is a schematic diagram of a data structure for correlating AMSA and defibrillation success to predicted outcomes for shocking a victim.

FIG. 1E is a table showing predictions of successful defibrillation for different AMSA threshold values in the instances of $1^{st}$ defibrillation attempts.

FIG. 1F is a table showing AMSA prior defibrillation for refractory and recurrent VF.

FIG. 1G is a table showing prediction of successful defibrillation for increasing AMSA threshold values in the instances of refractory VF.

DETAILED DESCRIPTION

In general, defibrillation is a common treatment for various arrhythmias, such as ventricular fibrillation (VF). However, there can be undesired side effects (e.g., heart tissue damage, skin burns, etc.) that follow an electrical shock. Other undesired side effects of electric shock therapy include unnecessary interruptions of chest compressions required to deliver the shock. It is therefore desirable to predict whether defibrillation will be successful in restoring a regular heartbeat following onset of an arrhythmic episode. Such a prediction is referred to as an "indicator of success" or, equivalently, a "success indication" within the context of the present disclosure. The prediction may be used so that a defibrillating shock is not provided when the chance of successful defibrillation is low, and instead a system will wait until the chance increases to an acceptable level. Such a determination can be used to alter care in an automatic and/or manual manner. In an automatic manner, a defibrillator may be made incapable of delivering a shock unless a success indication is above a determined amount. In a manual manner, the success indication may be shown to a rescuer, and the rescuer may determine whether to apply a shock or not based on the indication. A system may also integrate both—e.g., locking out the ability to provide a shock until a threshold level is reached, and then showing the relative likelihood of success above that value. The likelihood of success can be shown in various manners, such as by showing an actual percentage, or show two or more of a low, medium, or high likelihood of success, e.g., on a display of a defibrillator.

The present disclosure is directed to systems and methods for predicting whether defibrillation will be effective using amplitude spectrum area (AMSA) or any other appropriate Shock Prediction Algorithms (SPA) using analysis of electrocardiogram data, and adjusting such SPA predictions based on either the existence of prior defibrillation shocks as well as observations of a patient's reaction to those defibrillating shocks. In particular, it has been observed that victims of cardiac fibrillation will successfully defibrillate for lower AMSA threshold values if they have been previously successfully defibrillated during the same rescue session. Thus, rather than treating each shock as a discrete event in analyzing the probability of success, the techniques described here take into account prior shock deliveries, and the victim's observed response to those deliveries, in determining an AMSA value or other value that will indicate that a shock currently applied to the victim will likely be successful (or not) in defibrillating the victim. Such a determination may also be combined with determinations about trans-thoracic impedance (trans-thoracic impedance) of the patient, as discussed more fully below.

Figure 1A:
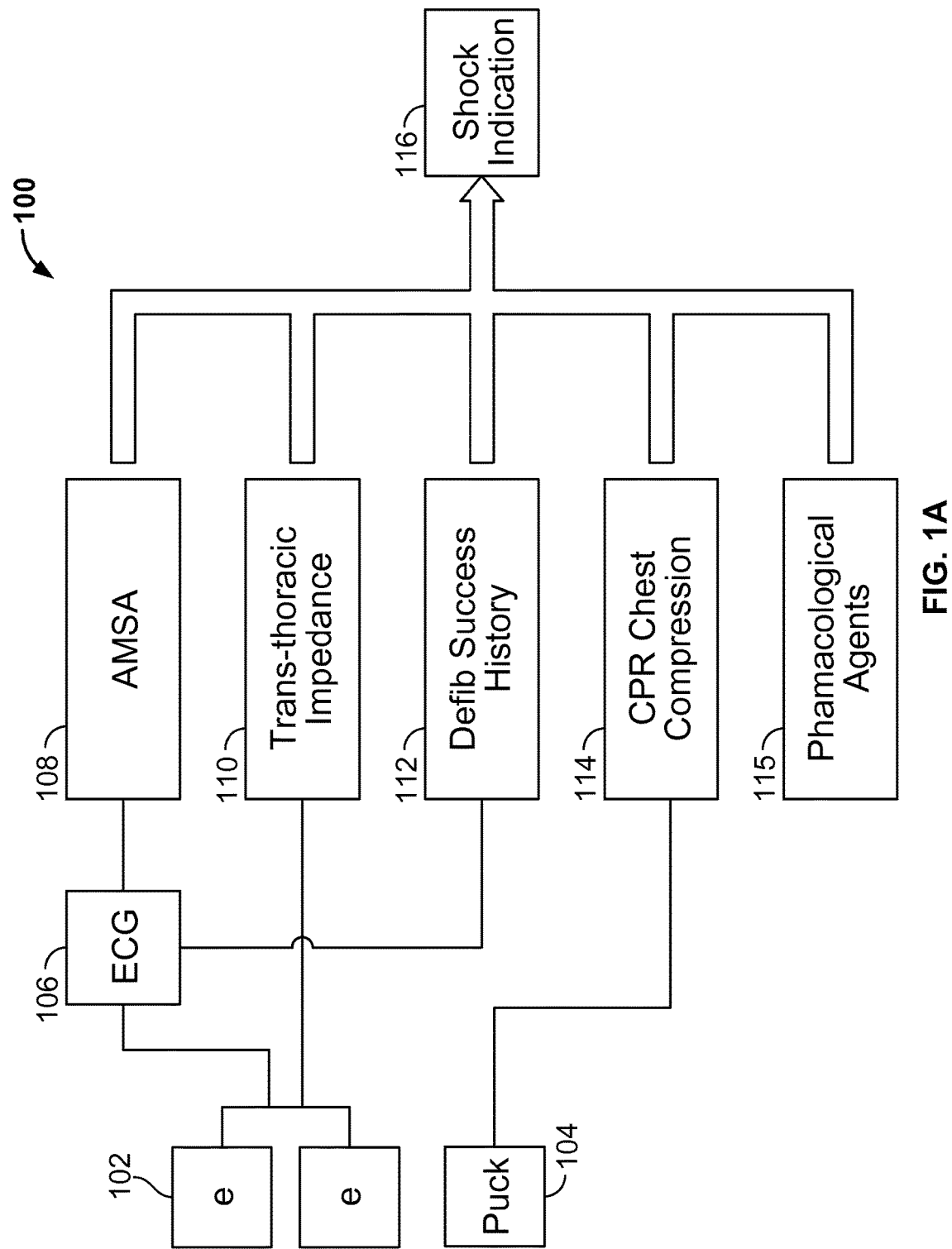
FIG. 1A shows schematically the combination of various types of data in making a determination about likely effectiveness of a defibrillating shock.

FIG. 1A shows schematically the combination 100 of various types of data in making a determination about likely effectiveness of a defibrillating shock. In this example, a shock indication 116 is the outcome of a decision process that may be performed by a defibrillator alone or in combination with one or more pieces of ancillary equipment (e.g., a computing device such as a smartphone carried by a healthcare provider). The shock indication 116 can be provided to part of the defibrillator, e.g., via an analog or digital signal that represents the indication, so that the part of the defibrillator may cause a shock feature to be executed or to cause it to be enabled so that it can be manually executed by an operator of the defibrillator. The shock indication may also or alternatively be provided to the rescuer so as to indicate that the rescuer can or should cause a defibrillating shock to be delivered. (In the context of this disclosure, a defibrillating shock is one of a level designed to cause defibrillation, but it does not need to be successful in causing the defibrillation.)

The relevant inputs may obtain at least some of their data from signals generated by a pair of electrodes 102 that may be adhere to a patient's torso—above one breast and below the other, for example, in a typical manner. The electrodes may include leads for obtaining ECG data and providing such data for analysis for a number of purposes. In addition, a CPR puck 104 may be placed on a patient's sternum and may deliver signals indicative of acceleration of the puck, and thus of up-down acceleration of the patient's sternum, which may be integrated so as to identify a depth of compression by the rescuer (and can also be used more simply to identify whether the patient is currently receiving chest compressions or not).

The electrodes 102 may be electrically connected to an ECG unit 106, which may be part of a portable defibrillator and may combine data from different leads (e.g., 8 leads) in a familiar manner to construct a signal that is representative of the patient's ECG pattern. Such an ECG signal is often used to generate a visual representation of the patient's ECG pattern on a screen of the defibrillator. The ECG-related data may also be analyzed in various ways to learn about the current condition of the patient, including in determining what sort of shock indication to provide to control the defibrillator or to display to a rescuer.

As one such example, ECG data may be provided to an AMSA analyzer 108, which may nearly continuously compute an AMSA number or similar indicator that represents ECG amplitude at particular different frequencies and/or frequency ranges. Generally, the goal is to identify a waveform in which amplitude of the VF signals is large, and in particular in the higher frequency ranges. Similarly, power spectrum area can be measured and its value can be used as an input that is alternative to, or in addition to, an AMSA value for purposes of making a shock indication.

A trans-thoracic impedance module 110 may also obtain information from sensors provided with the electrodes 102, which indicates the impedance of the patient between the locations of the two electrodes. The impedance can also be a factor in determining a shock indication as described in more detail below.

A defibrillation history success module 112 tracks the application of defibrillating shocks to the patient and whether they were successful in defibrillating the patient, and/or the level to which they were successful. For example, the module 112 may monitor the ECG waveform in time windows of various sizes for a rhythm that matches a profile of a "normal" heart rhythm, and if the normal rhythm is determined to be established for a predetermined time after the application of a defibrillating shock, the module 112 may register the existence of a successful shock. If a shock is applied and a normal rhythm is not established within a time window after the delivery of the shock, the module 112 can register a failed shock. In addition to registering a binary value of success/fail, the module may further analyze the ECG signal to determine the level of the success or failure and may, for example, assign a score to the chance of success of each shock, such as a normalized score between 0 (no chance of success) and total success (absolute certainty).

A CPR chest compression module 114 may receive signals about the motion of the puck 104 to determine whether chest compressions are currently being applied to the patient, and to determine the depth of such compressions. Such information may be used, for example, in giving a rescuer feedback about the pace and depth of the chest compressions (e.g., the defibrillator could generate a voice that says "push harder"). The presence of current chest compression activity may also signal the other components that a shock is not currently advisable, or that ECG data should be analyzed in a particular manner so as to remove residual artifacts in the ECG signal from the activity of the chest compressions.

Information about pharmacological agents 115 provided to a patient may also be identified and taken into account in providing a shock indication to a rescuer. Such information may be obtained manually, such as by a rescuer entering, via a screen on a defibrillator or on a tablet computer that communicates with the defibrillator, identifiers for the type of agent administered to a patient, the time of administration, and the amount administered. The information may also be obtained automatically, such as by instruments used to administer the particular pharmacological agents. The device that provides a shock indication may also take that information into account in identifying the likelihood that a shock will be successful if provided to the patient (e.g., by shifting an AMSA threshold for measuring shock success likelihood up or down), and for other relevant purposes.

One or more of the particular factors discussed here may then be fed to a shock indication module 116, which may combine them each according to an appropriate formula so as to generate a binary or analog shock indication. For example, any of the following appropriate steps may be taken: a score may be generated for each of the factors, the scores may normalized (e.g., to a 0 to 1 or 0 to 100 scale), a weighting may be applied to each of the scores to represent a determined relevance of that factor to the predictability of a shock outcome, the scores may be totaled or otherwise combined, and an indication can be determined such as a go/no go indication, a percentage of likely success, and other such indications.

Figure 1B:
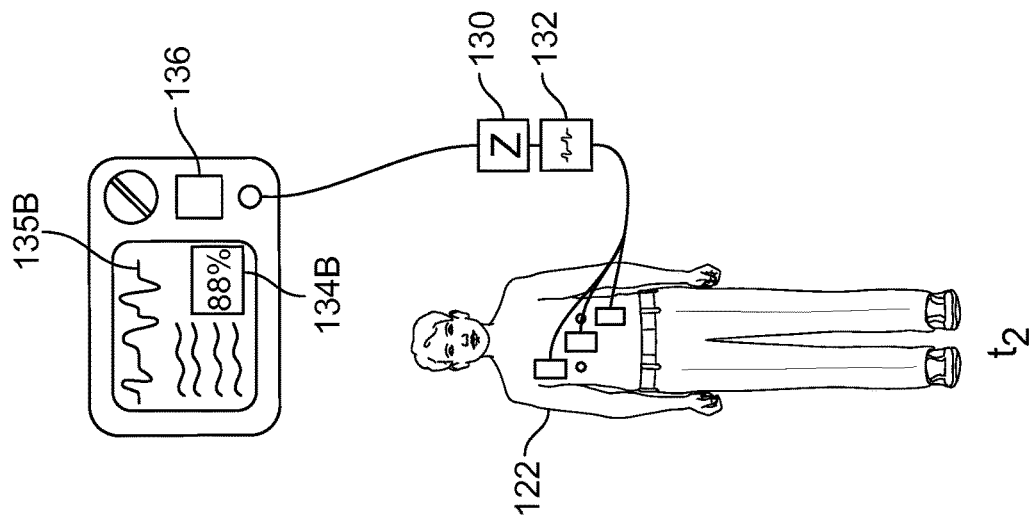
FIG. 1B shows a victim of a cardiac event being treated with a portable defibrillator.

FIG. 1B shows a victim 122 of cardiac arrest being cared for by a rescuer and defibrillator 124. The defibrillator 124 includes an electrode package 126 and a compression puck 128 generally coupled thereto. An example of such a defibrillator includes the AED PLUS automated external defibrillator or the AED PRO automated external defibrillator, both from ZOLL Medical Corporation of Chelmsford, Mass. Other embodiments of the defibrillator 124 are possible.

In the pictured example, the victim 122 is rendered prone due to an arrhythmic episode, and the electrode package 126 and the compression puck 128 are positioned on the torso of the victim 122 in an appropriate and known arrangement. In accordance with the present disclosure, the defibrillator 124, in tandem with one or both of the electrode package 126 and the compression puck 128, is configured to determine whether a defibrillation shock will be an effective measure to terminate the arrhythmic episode. The determination is generally based on prior success or failure of defibrillating shocks, one or more trans-thoracic impedance measurements, and one or more calculated AMSA values. As shown in the figure, the patient 122 is shown at two points in time—point t1 at which the patient has been defibrillated and is shown with his eyes open and a healthy ECG pattern 135A to indicate such successful defibrillation. At a later time t2, the patient has refibrillated and is shown with closed eyes to represent such a state, and with an erratic ECG trace 135B.

The defibrillator 104 is configured to acquire and manipulate both a trans-thoracic impedance signal 130 and an ECG signal 132 via the electrode package 126. As described in further detail below, a trans-thoracic impedance measurement ($\Omega$) is a parameter derived from the trans-thoracic impedance signal 130 that represents, among other things, thoracic fluid content. An AMSA value (V-Hz) is a parameter calculated by integrating the Fourier transform of the ECG signal 132 over a finite frequency range. The AMSA value is one form of calculation that represents a value of an ECG signal from a victim, while other SPA values may likewise be computed.

The defibrillator 124 is further configured to display an indicator 134 based on the defibrillating history (determined from ECG data), trans-thoracic impedance measurement(s) and AMSA value(s) obtained from the ECG signal 132, trans-thoracic impedance signal 130 and an ECG signal 132, respectively. The indicator 134 generally provides a perceptible cue that suggests whether or not a particular defibrillation event will likely terminate the arrhythmic episode of the victim 122. For example, for the patient 122 at time t1, the indicator 134 displays an X to indicate that no shock should be delivered to the patient 122. In contrast, at time t2, the indicator 134 displays a success indication of "88%," so a rescuer (not shown) can be instructed "Press to Shock" to apply a shock to the victim 122 via actuation of a control 136.

In this situation, the indication of an 88% likelihood of success was made by consulting data structure 130, which may be stored in memory of defibrillator 124 upon analysis that occurred around the time of t1. In particular, the defibrillator may analyze ECG data and an indicator provided by shock delivery circuitry in order to determine that a shock was delivered, and at a time soon after, the patient's heart rhythm entered a normal pattern, such that the defibrillator 123 may determine that the shock was a success at time T1. Upon making such a determination, the defibrillator may update data structure 130 to indicate that a successful defibrillation event has occurred during the rescue attempt. Other shocks may also be delivered, and the data structure 130 may be updated to reflect such events, and the success or failure of such events.

Embodiments other than display of a percentage likelihood for showing a shock indication are possible. For example, it will be appreciated that a success indication may be implemented as any type of perceptible feedback (e.g., haptic, audio, etc.) as desired. In certain implementations, the defibrillator 124 may make the determination of a likelihood of success without expressly notifying the rescuer, and may simply use the determination to determine when to tell the rescuer that a shock may be delivered. In other situations, the defibrillator 124 may explicitly indicate the likelihood of success, such as by showing a percentage likelihood, by showing less discrete gradations for success (e.g., poor, good, very good, and excellent), or by displaying a range of colors (e.g., with red indicating a poor chance and green indicating a good chance). The type of indication that is displayed may also differ based on a mode in which the defibrillator 124 is operating—for example, in a professional mode, more detail information may be provided, whereas in an AED mode, simpler information (a go/no go choice) may be presented.

In such manner then, the defibrillator may conduct a number of relatively complex calculations and may combine multiple factors in determining whether to allow a shock to be provided to a patient, or to encourage the application of such a shock by a rescuer.

FIG. 1C is a table showing examples relating AMSA to predicted likelihood of failure in defibrillating a victim who has or has not been previously defibrillated. The data was generally analyzed to determine the correlation between AMSA values and prior defibrillation success or failure with respect to success of subsequent defibrillation attempts.

The table shows the results of analysis of 1291 quality defibrillation events from 609 patients. AMSA was calculated for each such set of data based on a 1024 point ECG window that ended 0.5 seconds before each defibrillation. In the data, defibrillation was deemed successful when a spontaneous rhythm existed equal to or greater than 40 bpm and starting within 60 seconds from the shock, and also lasting for more than 30 seconds. A range of AMSA thresholds was calculated and evaluated for the data. The actual results shown in the other tables use the same or similar data, In summary of the data, where no prior defibrillation had occurred, the mean AMSA for successful shocks was 16.8 mV-HZ while the mean for unsuccessful shocks was 11.4 ($p<0.0001$). For subsequent shocks, the mean AMSA value fell to 15.0 for successful shocks and 7.4 for unsuccessful shocks.

Referring more specifically to the table itself, examples of data from defibrillation events were binned according to different AMSA values applied to the data as AMSA thresholds that would be used to determine whether to apply a subsequent shock. The first column of the table shows the different assigned AMSA values, while the second column shows the number of events that the particular chosen AMSA value correctly predicted, as compared to data indicating whether a defibrillation that was then applied was successful. The last column shows percentages with which the relevant AMSA value would have resulted in an accurate prediction if it had been used in the situations represented by the test data.

The upper section shows statistics for a first defibrillation attempt for each patient, while the lower section shows data for subsequent defibrillation attempts. The data indicates that lower AMSA values may provide more accurate predictions for subsequent defibrillations than for earlier defibrillations.

The upper portion of the table shows a comparison of aggregate mean AMSA values of first versus second shock, second versus third shock, etc. As the data indicates, such AMSA values generally fall from the first defibrillation attempt to the second, and to a lesser amount generally for each additional defibrillation attempt.

FIG. 1D is a schematic diagram of a data structure for correlating AMSA and prior defibrillation shocks to predicted outcomes for shocking a victim. The data structure here is greatly simplified in an effort to show how AMSA values and determinations about a number of prior shocks (successful or unsuccessful) may be used to predict whether another shock will succeed. This particular table shows correlations for prior shocks generally, though additional tables may be needed for identifying correlation for prior successful or unsuccessful shocks.

The table is shown in a format by which a program or human user could enter at one side of the table to select the value of one input variable, and then move across to the value of another variable, and obtain for an output a percentage likelihood of success, For example, the number of prior shocks are listed across the x-axis at the top of the table, while the percentage likelihood of success is shown along the right edge on the y-axis. The values in the body of the table are AMSA values that have been normalized to a 0 to 100 scale. The actual values are not intended to represent any actual outcome or actual numbers, but simply to indicate the interaction of the various values in coming to a conclusion about a likelihood of success.

Thus, for example, if a patient has received two defibrillating shocks, one would move to the third column of the table and then move down to a measured AMSA number—say 60. One would then move to the right edge to see the percentage likelihood of success—here, 70%. Values between those shown in the cells of the table can be rounded or interpolated or otherwise handled so as to provide likelihoods between each 10%. The likelihood of success identified from the data structure may then be used in various ways to implement the likelihood determination, such as providing the number for the likelihood determined to a microprocessor that can use it to determine whether to enable the shocking capability of a defibrillator and/or to display the value or a related value on the defibrillator for review by a rescuer. Where additional factors (e.g., trans-thoracic impedance) are to be considered, the table may take on additional dimensions, multiple tables may be used, or other techniques for generating a likelihood that is a composite of multiple different factors may be used.

FIG. 1E is a table showing predictions of successful defibrillation for different AMSA threshold values for instances of first defibrillation attempts. The threshold values are listed in the first column, and the cells to the right of each AMSA value indicate particular outcomes for shocks delivered at those AMSA values for initial shocks.

The particular values shown include sensitivity, specificity, positive predictive value (PPV), negative predictive value (NPV), and accuracy, which are statistical measures of the performance of AMSA prediction for shock outcome. Sensitivity indicates the proportion of actual shock successes that were correctly identified. For example, if there were 100 shock successes, and 60 of the 100 were identified by an AMSA threshold of 10 mVHz, then the sensitivity is 0.6 using 10 mVHz as the AMSA threshold. Specificity represents the proportion of shock failures that were correctly identified by the particular AMSA value. PPV is the shock success rate. For example, if 10 mVHz was used as the AMSA threshold to deliver shocks and 100 shocks were delivered with 60 defibrillation successes, PPV=0.6. NPV is the shock failure rate. For example, if 10 mVHz was used as the AMSA threshold for the 100 cases, with AMSA<10 failing to shock, there are 90 cases of failed shock, or NPV=0.9. Accuracy is the proportion of true results (correctly predicted as shock success and shock failure by AMSA) in the total patient population.

FIG. 1F is a table showing AMSA prior defibrillation for refractory and recurrent VF. In particular, the table shows AMSA values that were measured before a defibrillating shock was delivered, and then correlated to whether the shock was successful or not. The first row shows the mean AMSA for all shocks, successful or unsuccessful, broken out by whether refractory VF was present or recurrent VF was present (where mean+/−SEM is shown for each of the values in the table). The second row shows the AMSA, for both refractory and recurrent VF, where the result of the shock was a successful defibrillation, while the third row shows corresponding values for shocks that did not successfully defibrillate. The final row shows the shocks that were successful in defibrillating the subject, both in terms of percentage and numbers. As can be seen, the level of success was much higher for recurrent VF than for refractory VF, and the AMSA was also higher.

FIG. 1G is a table showing prediction of successful defibrillation for increasing AMSA threshold values in the instances of refractory VF. The parameters shown in the table are similar to those shown for FIG. 1E.

Figure 1B:
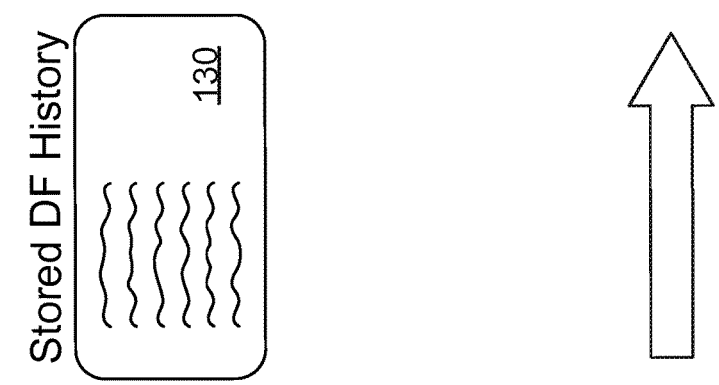
Figure 2:
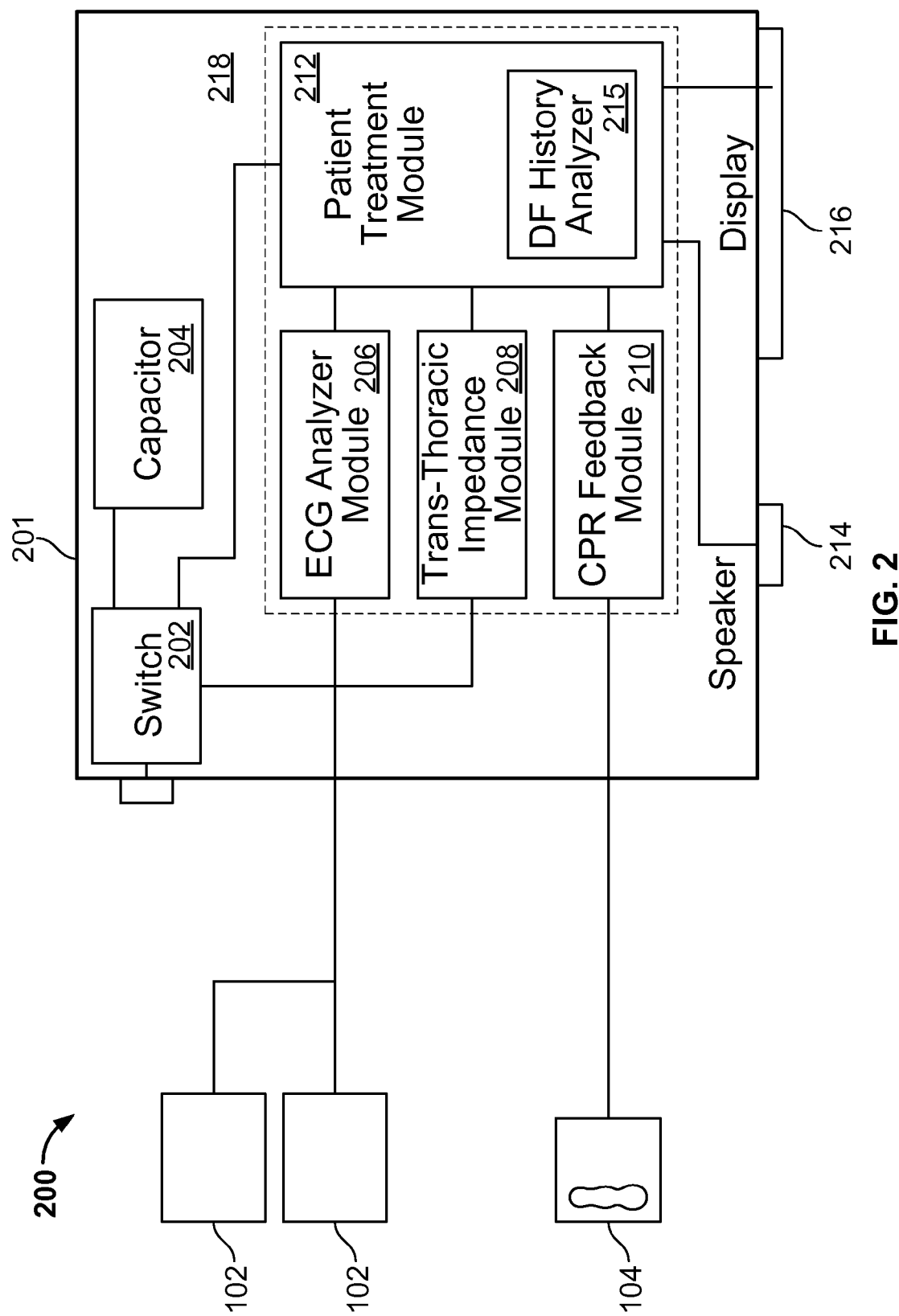
FIG. 2 is a schematic block diagram that shows a defibrillator with an electrode package and compression puck.

Referring now to FIG. 2, a schematic block diagram 200 shows an example defibrillator 201, along with the example electrode package 102 and compression puck 106, of FIG. 1 in more detail. In general, the defibrillator 201, and optionally one or more of the electrode package 104 and compression puck 106, defines an apparatus for administering care to a patient, subject, or individual (e.g., victim 102) who requires cardiac assistance.

The defibrillator 201 includes a switch 202 and at least one capacitor 204 for selectively supplying or applying a shock to a subject. The defibrillator 201 further includes an ECG analyzer module 206, a trans-thoracic impedance module 208, a CPR feedback module 210 that controls frequency and magnitude of chest compressions applied to a subject, a patient treatment (PT) module 212 (which includes a defibrillation history analyzer 215), a speaker 214, and a display 216. In this example, the ECG analyzer module 206, trans-thoracic impedance module 208, CPR feedback module 210, and patient treatment (PT) module 212 are grouped together as a logical module 218, which may be implemented by one or more computer processors. For example, respective elements of the logical module 218 can be implemented as: (i) a sequence of computer implemented instructions executing on at least one computer processor of the defibrillator 201; and (ii) interconnected logic or hardware modules within the defibrillator 201, as described in further detail below in connection with FIG. 6.

In the example of FIG. 2, the electrode package 104 is connected to the switch 202 via port on the defibrillator 201 so that different packages may be connected at different times. The electrode package may also be connected through the port to ECG analyzer module 206, and trans-thoracic impedance module 208.

The compression puck 106 is connected, in this example, to the CPR feedback module 210. In one embodiment, the ECG analyzer module 206 is a component that receives an ECG (e.g., ECG signal 112). Similarly, the trans-thoracic impedance module 208 is a component that receives transsthoracic impedance (e.g., trans-thoracic impedance signal 110). Other embodiments are possible The patient treatment module 212 is configured to receive an input from each one of the ECG analyzer module 206, trans-thoracic impedance module 208, and CPR feedback module 210. The patient treatment module 212 uses inputs as received from at least the ECG analyzer module 206 and trans-thoracic impedance module 208 to predict whether a defibrillation event will likely terminate an arrhythmic episode. For example, ECG data can be used both to determine AMSA values for a patient, and also determine whether shocks are effective or not so that such information can be saved and used to identify likelihoods that subsequent shocks will be effective). In this manner, the patient treatment module 212 uses information derived from both an ECG signal (both for AMSA and for adjusting the AMSA value) and transthoracic impedance measurement to provide a determination of a likelihood of success for delivering a defibrillating shock to a subject.

The patient treatment module 212 is further configured to provide an input to each one of the speaker 214, display 216, and switch 202. In general, input provided to the speaker 214 and a display 216 corresponds to either a success indication or a failure indication regarding the likelihood of success for delivering a shock to the subject. In one embodiment, the difference between a success indication and a failure indication is binary and based on a threshold. For example, a success indication may be relayed to the display 216 when the chances corresponding to a successful defibrillation event is greater than 75%. In this example, the value "75%" may be rendered on the display 216 indicating a positive likelihood of success. When a positive likelihood of success is indicated, the patient treatment module 212 enables the switch 202 such that a shock may be delivered to a subject.

The patient treatment module 212 may also implement an ECG analyzer for generating an indication of heart rate for the patent, for generating an indication of heart rate variability for the patent, an indication of ECG amplitude for the patent, and/or an indication of a first or second derivative of ECG amplitude for the patient. The indication of ECG amplitude can include an RMS measurement, measured peak-to-peak, peak-to-trough, or an average of peak-to-peak or peak-to-trough over a specified interval. Such indications obtained by the ECG analyzer may be provided to compute an AMSA value for the patient and/or can be used in combination with a computed AMSA value so as to generate some derivative indication regarding whether a subsequent shock is likely or unlikely to be effective (and the degree, e.g., along a percentage scale, of the likelihood).

In another embodiment, likelihood of a successful defibrillation event may be classified into one of many possible groups such as, for example, low, medium, and high likelihood of success. With a "low" likelihood of success (e.g., corresponding to a successful defibrillation event is less than 50%), the patient treatment module 212 disables the switch 202 such that a shock cannot be delivered to a subject. With a "medium" likelihood of success (e.g., corresponding to a successful defibrillation event is greater than 50% but less than 75%), the patient treatment module 212 enables the switch 202 such that a shock may be delivered to a subject, but also renders a warning on the display 216 that the likelihood of success is questionable. With a "high" likelihood of success (e.g., corresponding to a successful defibrillation event is greater than or equal to 75%), the patient treatment module 212 enables the switch 202 such that a shock may be delivered to a subject, and also renders a cue on the display 216 indicating that the likelihood of success is very good. Still other embodiments are possible.

Thus, the system 200 may provide, in a portable electric device (e.g., a battery-operated device) the capability to analyze a number of inputs and to identify a variety of factors from those inputs, where the factors can then be combined to provide a flexible, intelligent determination of likely success.

Figure 3:
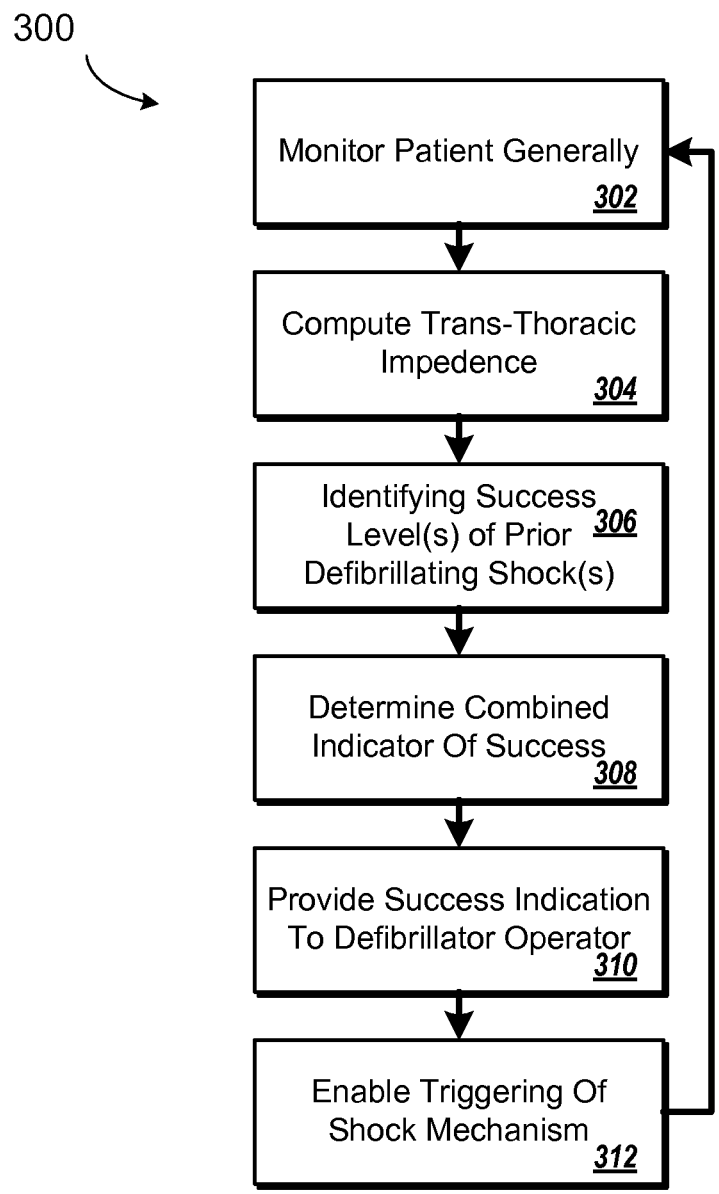
FIG. 3 is a flow chart of a process for providing a user with feedback regarding a likelihood that a defibrillating shock will be successful.

Referring now to FIG. 3, an example method 300 is shown for administering care to an individual requiring cardiac assistance. In one embodiment, the method 300 is implemented by the example defibrillators described above in connection with FIGS. 1B and 2. However, other embodiments are possible.

At a step 302, at least one of an ECG signal (e.g., ECG signal 112) and a trans-thoracic impedance signal (e.g., trans-thoracic impedance signal 110) of the subject receiving cardiac care is monitored. In general, an individual receiving cardiac care includes the individual at any time during a cardiac event, including whether or not individual is receiving active care (e.g., chest compressions).

At a step 304, a trans-thoracic impedance value is extracted from the trans-thoracic impedance signal as monitored at step 302. Additionally, at step 304, an AMSA value can be calculated from the ECG signal as monitored at step 302 by integrating the Fourier transform (e.g., FFT) of the ECG signal over a finite frequency range. Example frequency content of an arrhythmic ECG signal generally ranges between about 1 Hz to about 40 Hz, with amplitude of about 50 mV or less. An example of an AMSA value calculated from such a signal ranges between about 5 mV-Hz to about 20 mV-Hz. It will be appreciated however that this is only an example, and that the magnitude and spectra of an ECG signal ranges greatly.

At a step 306, the process identifies success levels of prior shocks applied to the patient during the cardiac event. Such determination may occur in various manners. At a simplest level, the process may simply track the number of times a defibrillating shock has been provided to the patient. In more complex implementations, the process may identify how many attempts were successful and how many were not, and in a slightly more complex implementation, may identify which were successful and which were not (e.g., because subsequent steps may perform more accurately by weighting the influence of different ones of the prior defibrillations in different ways). In yet more complex systems, the degrees of prior success can be determined, which may include determining how close the patient's defibrillated heart rate was to a predetermined rate (either a particular rate or a range of rates) or how consistent the rate was over time, or a combination of both to generate a score for the quality of the defibrillation. Other examples of physiologic measure that may be useful for generating a score may be pulse oximetry, capnography, blood pressure, or other pulse or blood flow detection methods.

As one such example, scoring the ECG quality of the post-shock ECG rhythm may occur by giving heart rates in the range of 50-90 BPM a higher score than those above or below that range (with the score decreasing the further from that range the heart rates were). More complex scoring systems could additionally or alternatively be used, such as using a windowing function that weights a heart rate of a patient to generate a normalized score. Such a windowing functions might be a Hamming window or a Tukey window with a rectangle width that is flat from 50-90 BPM. In each such situation, the data gathered for each defibrillation may be saved so that it can be accessed in preparation for determining and providing identifications of likely success for later defibrillations.

At step 308, the process determines a combined indicator of success that includes an indication from trans-thoracic impedance and an indication from an ECG reading, such as an AMSA indication, and is modified appropriately to reflect data about prior successes or failure in defibrillation. The combined indicator may be determined by inputting a trans-thoracic impedance value, an AMSA value, and a count or other indicator of prior success or failure, into a function or look-up table, or may be determined without a need to compute both or all values first, such as by taking inputs indicative of all values and computing a predictor of success directly from such indicative values. Alternatively to using a table to calculate the predictive score, the use of logistic regression may be used with a logistic regression equation, with inputs to the equation with, e.g. ECG rhythm type, ECG rate, transthoracic impedance, prior shocks, etc. Neural network or fuzzy logic methods or other non-linear decision-making methods may also be used.

At box 310, a success indication is provided to a defibrillator operator. The indication may take a variety of forms. For example, the ability of the defibrillator to deliver a shock may be enabled when the indicator of success is higher than a threshold level. Also, the user may be notified that the defibrillator can provide a shock, and may be prompted to push a physical button to cause the shock to be delivered.

The user may also be provided with more detail about the success indication. For example, the user may be shown a percentage number that indicates a likelihood in percent that the shock will be successful. Alternatively, or in addition, the user may be show a less granular level of an indication, such as a value of "excellent," "good," and "poor" to indicate to the user what the likelihood of successful defibrillation is.

At box 312, the trigger mechanism is enabled on the defibrillator, as discussed above. In certain instances, such a feature may be enabled whenever a shockable rhythm is observed for a patient. In other circumstances, the enabling may occur only when the combined indication discussed above exceeds a threshold value for indicating that a shock will be successful in defibrillating the patient.

An arrow is shown returning to the top of the process to indicate that the process here is in ways continuous and in ways repeated. In particular, ECH signals are gathered continuously, as are other types of data. And the process repeatedly tries to identify whether a shock can or should be provided, and the order and timing of the steps in that cycling may be dictated by standards as adjusted by a medical director or other appropriate individual responsible for the deployed defibrillator.

Figure 4A:
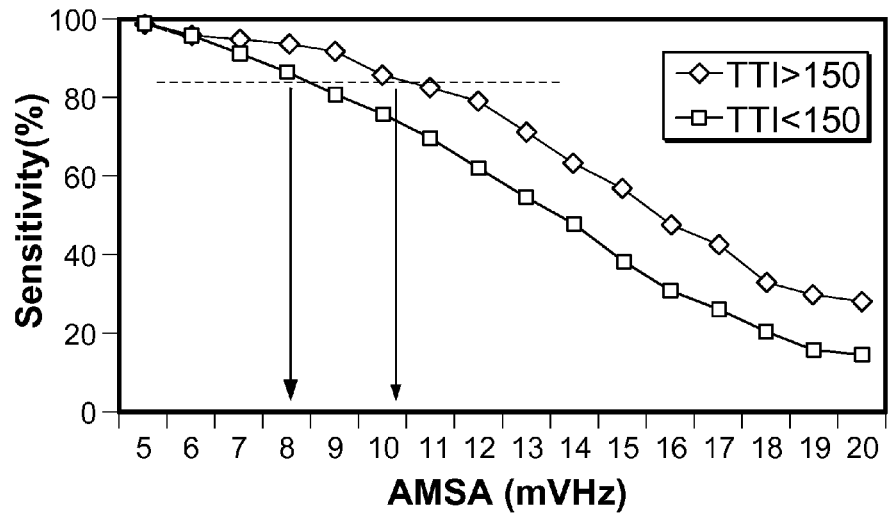
FIGS. 4A and 4B are graphs showing relationships between patient outcome and AMSA threshold values for groups of patients having different trans-thoracic impedance values.

FIG. 4A shows a plot of positive predictive value (%) versus AMSA threshold (mv-Hz) for a first set of subjects having a trans-thoracic impedance measured greater than 150 ohms and a second set of subjects having a trans-thoracic impedance measured less than 150 ohms. As shown by the comparative data, the first set of subjects generally has a greater positive predictive value for a given AMSA threshold. In both cases, positive predictive value generally increases with increasing AMSA threshold. Thus, an indication of success for a patient having a low impedance may be provided when the AMSA value is lower, than for a comparable AMSA value from a high impedance patient. Or, where a percentage likelihood of success is shown, the displayed percentage for a particular AMSA value may be higher for a low impedance patient as compared to a high impedance patient—at least with the range of AMSA values from 5-20 my-HZ.

Figure 4B:
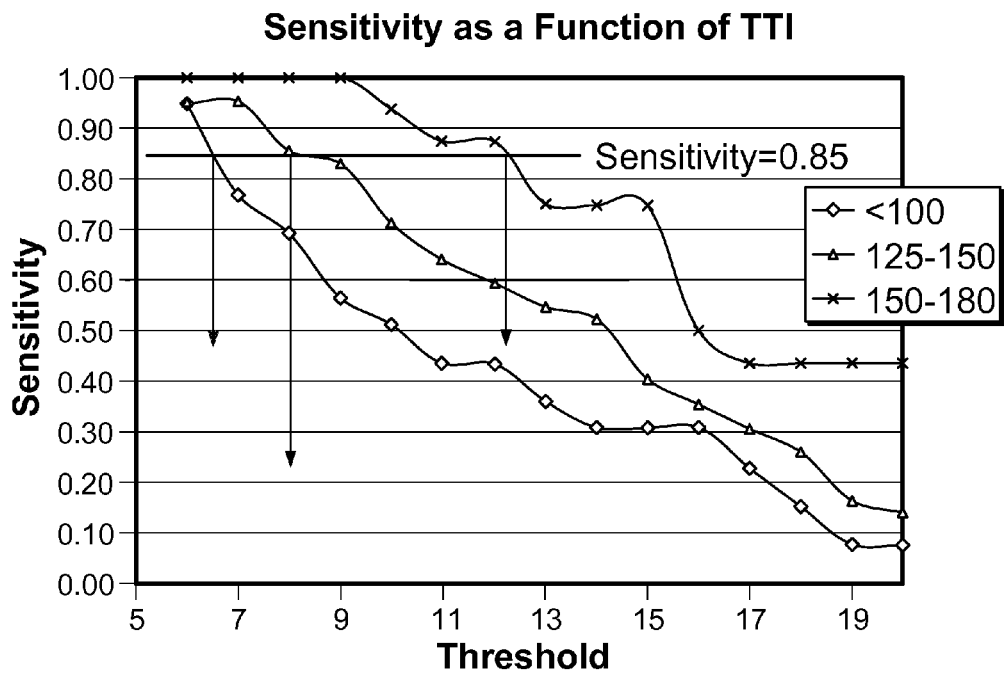

FIG. 4B shows a plot of sensitivity (unit-less) versus AMSA threshold (mv-Hz) for a first set of subjects having a trans-thoracic impedance measured less than 100 ohms, a second set of subjects having a trans-thoracic impedance measured between 125 ohms and 150 ohms, and a third set of subjects having a trans-thoracic impedance measured between 150 ohms and 180 ohms. As shown by the comparative data, AMSA threshold generally increases, for a given specificity, with increasing trans-thoracic impedance.

Figure 5A:
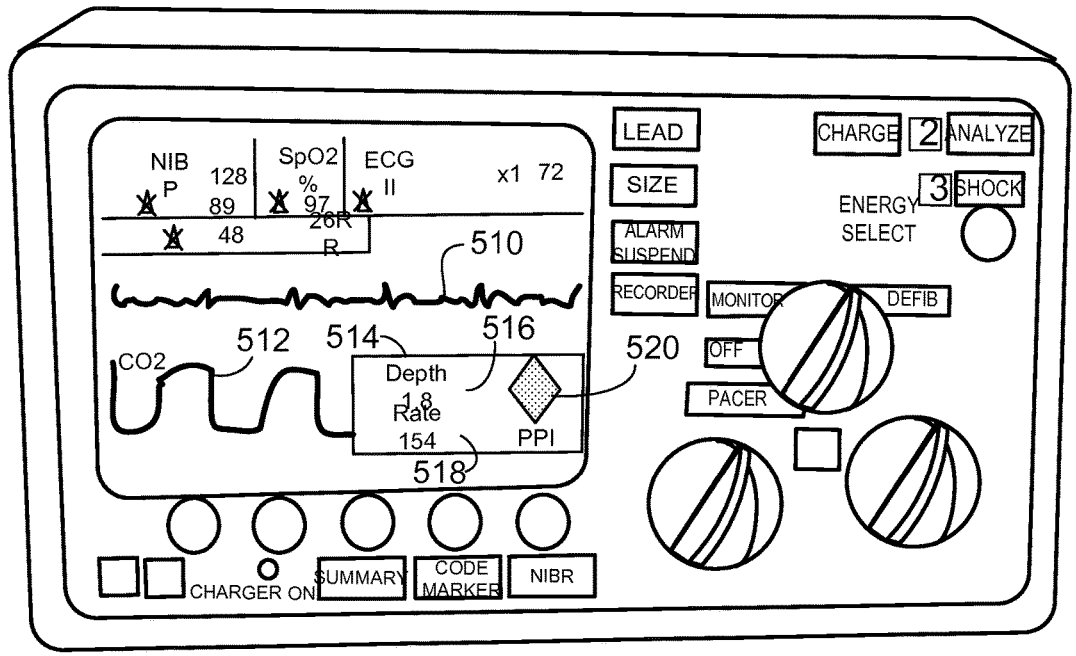
FIGS. 5A and 5B illustrate a defibrillator showing certain types of information that can be displayed to a rescuer.

FIG. 5A shows a defibrillator showing certain types of information that can be displayed to a rescuer. In the figure, a defibrillation device 500 with a display portion 502 provides information about patient status and CPR administration quality during the use of the defibrillator device. As shown on display 502, during the administration of chest compressions, the device 500 displays information about the chest compressions in box 514 on the same display as is displayed a filtered ECG waveform 510 and a CO2 waveform 512 (alternatively, an SpO2 waveform can be displayed).

During chest compressions, the ECG waveform is generated by gathering ECG data points and accelerometer readings, and filtering the motion-induced (e.g., CPR-induced) noise out of the ECG waveform. Measurement of velocity or acceleration of chest compression during chest compressions can be performed according to the techniques taught by U.S. Pat. No. 7,220,335, titled Method and Apparatus for Enhancement of Chest Compressions During Chest Compressions, the contents of which are hereby incorporated by reference in their entirety.

Displaying the filtered ECG waveform helps a rescuer reduce interruptions in CPR because the displayed waveform is easier for the rescuer to decipher. If the ECG waveform is not filtered, artifacts from manual chest compressions can make it difficult to discern the presence of an organized heart rhythm unless compressions are halted. Filtering out these artifacts can allow rescuers to view the underlying rhythm without stopping chest compressions.

The CPR information in box 514 is automatically displayed when compressions are detected by a defibrillator. The information about the chest compressions that is displayed in box 514 includes rate 518 (e.g., number of compressions per minute) and depth 516 (e.g., depth of compressions in inches or millimeters). The rate and depth of compressions can be determined by analyzing accelerometer readings. Displaying the actual rate and depth data (in addition to, or instead of, an indication of whether the values are within or outside of an acceptable range) can also provide useful feedback to the rescuer. For example, if an acceptable range for chest compression depth is 1.5 to 2 inches, providing the rescuer with an indication that his/her compressions are only 0.5 inches can allow the rescuer to determine how to correctly modify his/her administration of the chest compressions (e.g., he or she can know how much to increase effort, and not merely that effort should be increased some unknown amount).

The information about the chest compressions that is displayed in box 514 also includes a perfusion performance indicator (PPI) 520. The PPI 520 is a shape (e.g., a diamond) with the amount of fill that is in the shape differing over time to provide feedback about both the rate and depth of the compressions. When CPR is being performed adequately, for example, at a rate of about 100 compressions per minute (CPM) with the depth of each compression greater than 1.5 inches, the entire indicator will be filled. As the rate and/or depth decreases below acceptable limits, the amount of fill lessens. The PPI 520 provides a visual indication of the quality of the CPR such that the rescuer can aim to keep the PPI 520 completely filled.

As shown in display 500, the filtered ECG waveform 510 is a full-length waveform that fills the entire span of the display device, while the second waveform (e.g., the CO2 waveform 512) is a partial-length waveform and fills only a portion of the display. A portion of the display beside the second waveform provides the CPR information in box 514. For example, the display splits the horizontal area for the second waveform in half, displaying waveform 512 on left, and CPR information on the right in box 514.

The data displayed to the rescuer can change based on the actions of the rescuer. For example, the data displayed can change based on whether the rescuer is currently administering CPR chest compressions to the patient. Additionally, the ECG data displayed to the user can change based on the detection of CPR chest compressions. For example, an adaptive filter can automatically turn ON or OFF based on detection of whether CPR is currently being performed. When the filter is on (during chest compressions), the filtered ECG data is displayed and when the filter is off (during periods when chest compressions are not being administered), unfiltered ECG data is displayed. An indication of whether the filtered or unfiltered ECG data is displayed can be included with the waveform.

Also shown on the display is a reminder 521 regarding "release" in performing chest compression. Specifically, a fatigued rescuer may begin leaning forward on the chest of a victim and not release pressure on the sternum of the victim at the top of each compression. This can reduce the perfusion and circulation accomplished by the chest compressions. The reminder 521 can be displayed when the system recognizes that release is not being achieved (e.g., signals from an accelerometer show an "end" to the compression cycle that is flat and thus indicates that the rescuer is staying on the sternum to an unnecessary degree). Such a reminder can be coordinated with other feedback as well, and can be presented in an appropriate manner to get the rescuer's attention. The visual indication may be accompanied by additional visual feedback near the rescuer's hands, and by a spoken or tonal audible feedback, including a sound that differs sufficiently from other audible feedback so that the rescuer will understand that release (or more specifically, lack of release) is the target of the feedback.

Figure 5B:
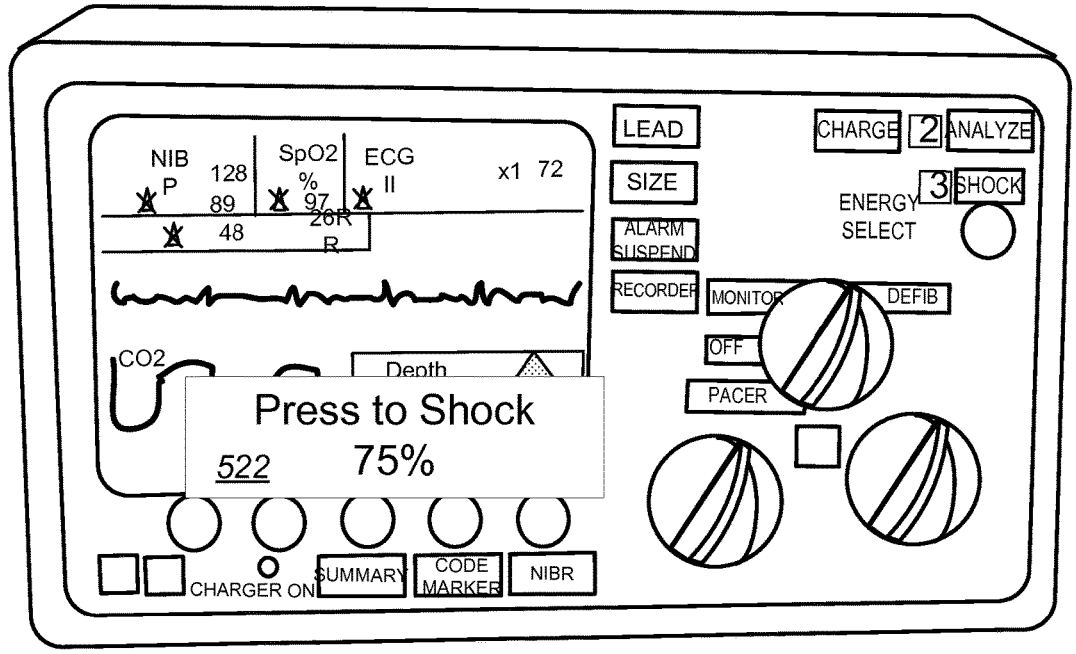

FIG. 5B shows the same defibrillator, but with an indicator box 522 now shown across the bottom half of the display and over the top of information that was previously displayed to display a success indication of "75%." Similar to the display 216 as described above, the indicator box 522 can generally convey a success indication or a failure indication regarding the likelihood of success for delivering a shock to a subject. The success indication can be generated using any combination of the techniques discussed above, including AMSA values, measures of prior effectiveness or ineffectiveness of prior defibrillating shocks, and trans-thoracic impedance.

In certain instances, one or more of the inputs used for determining a likelihood that a future shock will be successful, will not be available. For example, at times it may not be possible to calculate AMSA accurately when CPR compressions are occurring. Or perhaps a system is receiving values for trans-thoracic impedance that are not possible, which would indicate a problem with the sensors measuring such impedance or other similar problems. In such situations, the score that is generated to indicate a likelihood of success may be switched to a score that depends only on n−1 inputs (where n is the optimal number of inputs, and n−1 represents the removal of one of the inputs). Thus, the system may be adaptive to problems with particular ones of the inputs that indicate a likelihood of success, yet the system may still determine a likelihood of success that is as accurate as possible given the inputs that are available.

In the example shown, the success indication is textual; however the success indication (and/or failure indication) can generally be implemented as any type of perceptible feedback. For example, tone, color, and/or other perceptible visual effects can be rendered or otherwise displayed to a user via the indicator box. For example, the characters "75%" may be highlighted or otherwise distinguished in a bold color, and the phrase "Press to Shock" may blink at least intermittently to convey a sense of urgency with respect to a pending shock. Other embodiments are possible.

Figure 6A:
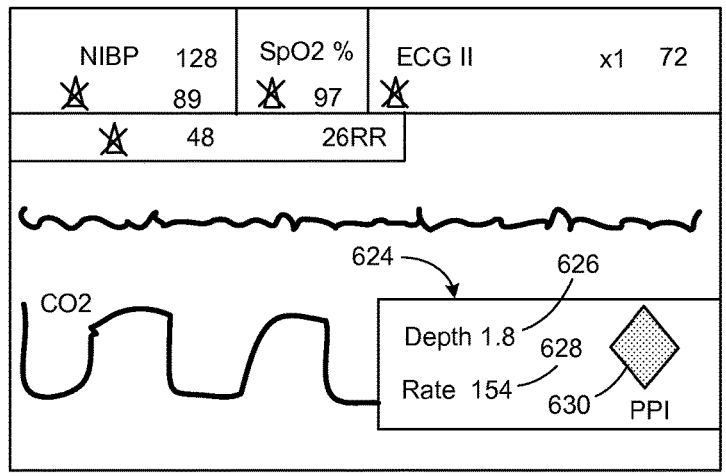
FIGS. 6A-6C show screenshots of a defibrillator display that provides feedback concerning chest compressions performed on a victim.
Figure 6B:
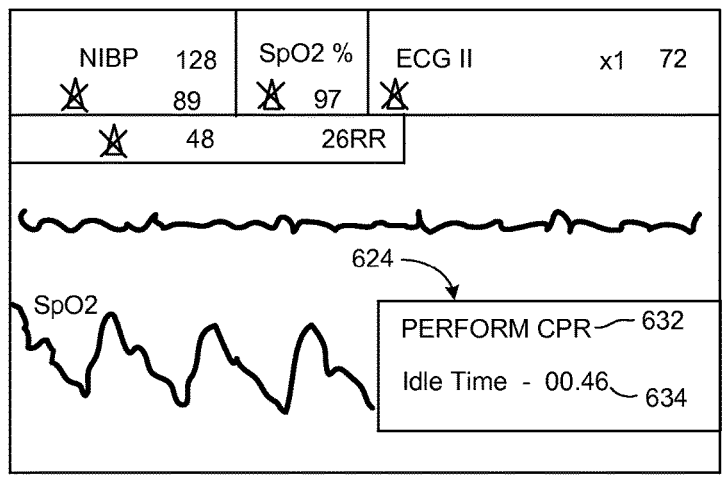
Figure 6C:
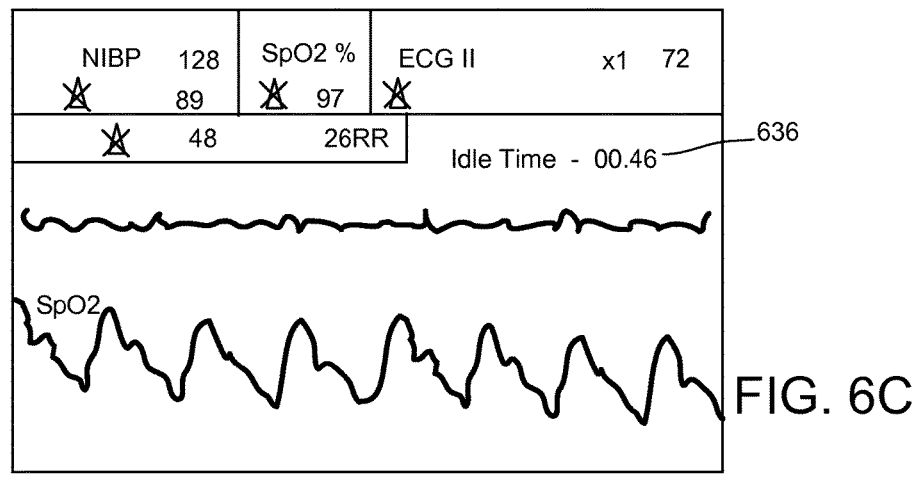

FIGS. 6A-6C show example screens that may be displayed to a rescuer on a defibrillator. Each of the displays may be supplemented with an indicator-like box 522 in FIG. 5B when the defibrillator makes a determination as to the likelihood of success for delivering a shock to a subject.

FIG. 6A shows exemplary information displayed during the administration of CPR chest compressions, while FIGS. 6B and 6C show exemplary information displayed when CPR chest compressions are not being sensed by the defibrillator. The defibrillator automatically switches the information presented based on whether chest compressions are detected. An exemplary modification of the information presented on the display can include automatically switching one or more waveforms that the defibrillator displays. In one example, the type of measurement displayed can be modified based on the presence or absence of chest compressions. For example, $CO_2$ or depth of chest compressions may be displayed (e.g., a $CO_2$ waveform 620 is displayed in FIG. 6A) during CPR administration, and upon detection of the cessation of chest compressions, the waveform can be switched to display an $SpO_2$ or pulse waveform (e.g., an $SpO_2$ waveform 622 is displayed in FIG. 6B).

Another exemplary modification of the information presented on the display can include automatically adding/removing the CPR information from the display upon detection of the presence or absence of chest compressions. As shown in FIG. 6A, when chest compressions are detected, a portion 624 of the display includes information about the CPR such as depth 626, rate 628, and PPI 630. As shown in FIG. 6B, when CPR is halted and the system detects the absence of CPR chest compressions, the defibrillator changes the CPR information in the portion 624 of the display, to include an indication 632 that the rescuer should resume CPR, and an indication 634 of the idle time since chest compressions were last detected. In a similar manner, when the defibrillator determines that rescuers should change, the label 632 can change to a message such as "Change Who is Administering CPR." In other examples, as shown in FIG. 6C, when CPR is halted, the defibrillation device can remove the portion of the display 624 previously showing CPR data and can display a full view of the second waveform. Additionally, information about the idle time 636 can be presented on another portion of the display.

Figure 7A:
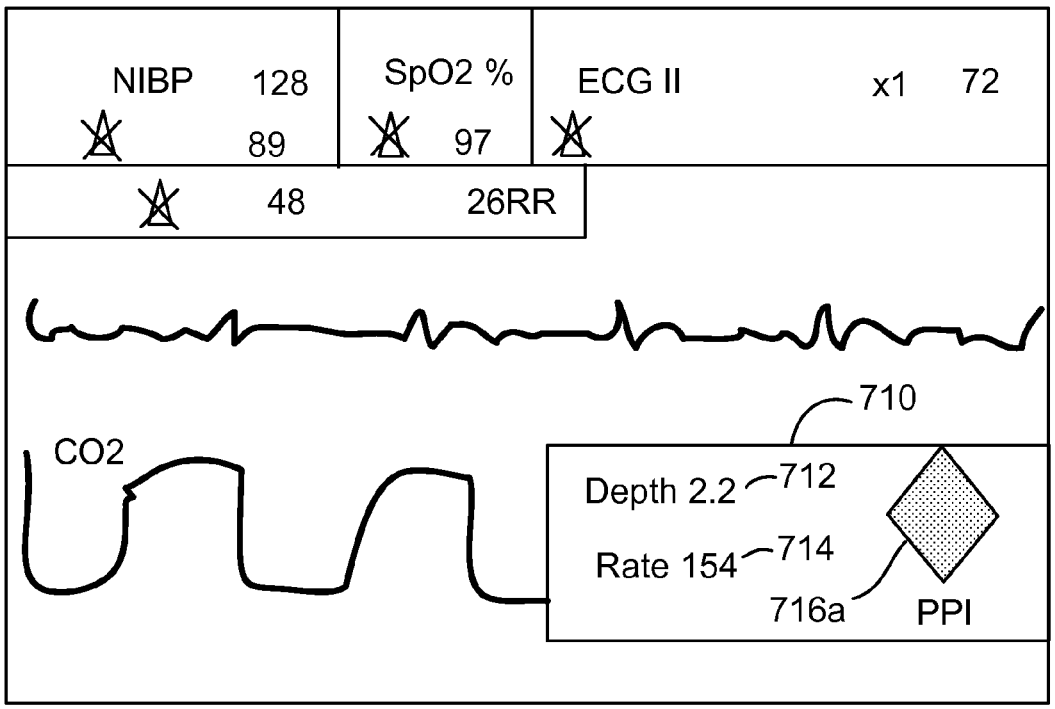
FIGS. 7A and 7B show screenshots providing feedback regarding a perfusion index created from chest compressions.
Figure 7B:
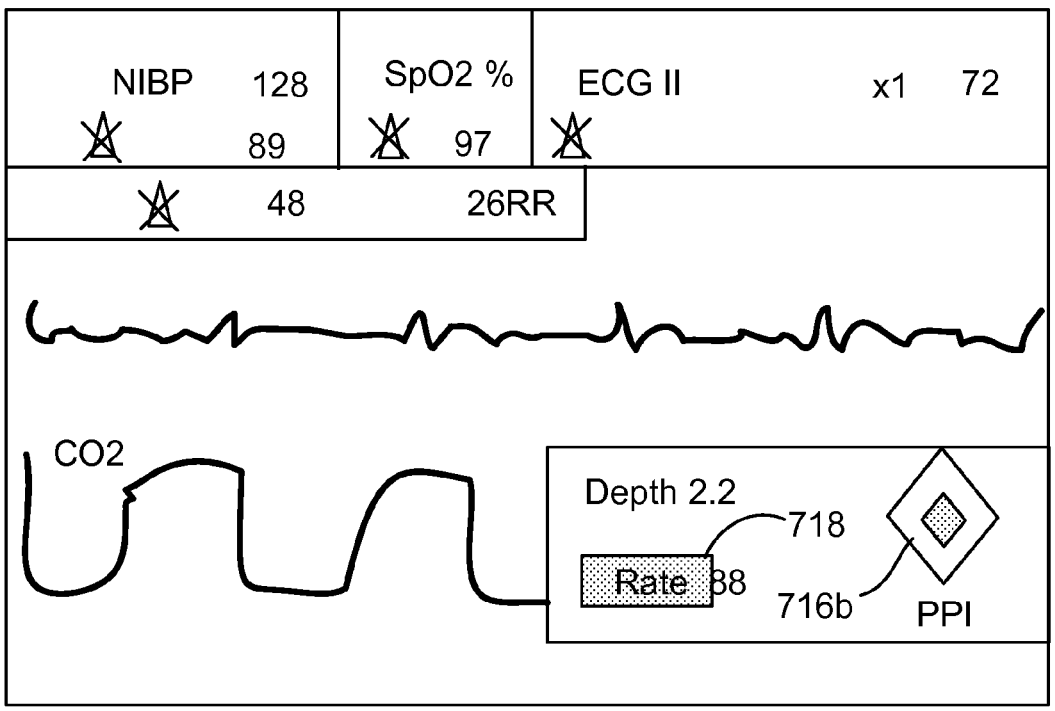

FIGS. 7A and 7B show defibrillator displays that indicate to a rescuer levels of perfusion being obtained by chest compressions that the rescuer is performing. FIG. 7A shows exemplary data displayed during the administration of CPR chest compressions when the CPR quality is within acceptable ranges, while FIG. 7B shows modifications to the display when the CPR quality is outside of the acceptable range.

In the example shown in FIG. 7B, the rate of chest compressions has dropped from 154 compressions per minute (FIG. 7A) to 88 compressions per minute. The defibrillator device determines that the compression rate of 88 compressions per minute is below the acceptable range of greater than 100 compressions per minute. In order to alert the user that the compression rate has fallen below the acceptable range, the defibrillator device provides a visual indication 718 to emphasize the rate information. In this example, the visual indication 718 is a highlighting of the rate information. Similar visual indications can be provided based on depth measurements when the depth of the compressions is shallower or deeper than an acceptable range of depths. Also, when the change in rate or depth indicates that a rescuer is becoming fatigued, the system may display a message to switch who is performing the chest compressions, and may also emit aural or haptic feedback to the same effect.

In the examples shown in FIGS. 7A and 7B, a perfusion performance indicator (PPI) 716 provides additional information about the quality of chest compressions during CPR. The PPI 716 includes a shape (e.g., a diamond) with the amount of fill in the shape differing based on the measured rate and depth of the compressions. In FIG. 7A, the depth and rate fall within the acceptable ranges (e.g., at least 100 compressions/minute (CPM) and the depth of each compression is greater than 1.5 inches) so the PPI indicator 716a shows a fully filled shape. In contrast, in FIG. 7B, when the rate has fallen below the acceptable range, the amount of fill in the indicator 716b is lessened such that only a portion of the indicator is filled. The partially filled PPI 716b provides a visual indication of the quality of the CPR is below an acceptable range.

As noted above with respect to FIG. 5A, in addition to measuring information about the rate and depth of CPR chest compressions, in some examples the defibrillator provides information about whether the rescuer is fully releasing his/her hands at the end of a chest compression. For example, as a rescuer tires, the rescuer may begin leaning on the victim between chest compressions such that the chest cavity is not able to fully expand at the end of a compression. If the rescuer does not fully release between chest compressions the quality of the CPR can diminish. As such, providing a visual or audio indication to the user when the user does not fully release can be beneficial. In addition, such factors may be included in a determination of whether the rescuer's performance has deteriorated to a level that the rescuer should be instructed to permit someone else perform the chest compressions, and such information may be conveyed in the various manners discussed above.

Figure 8A:
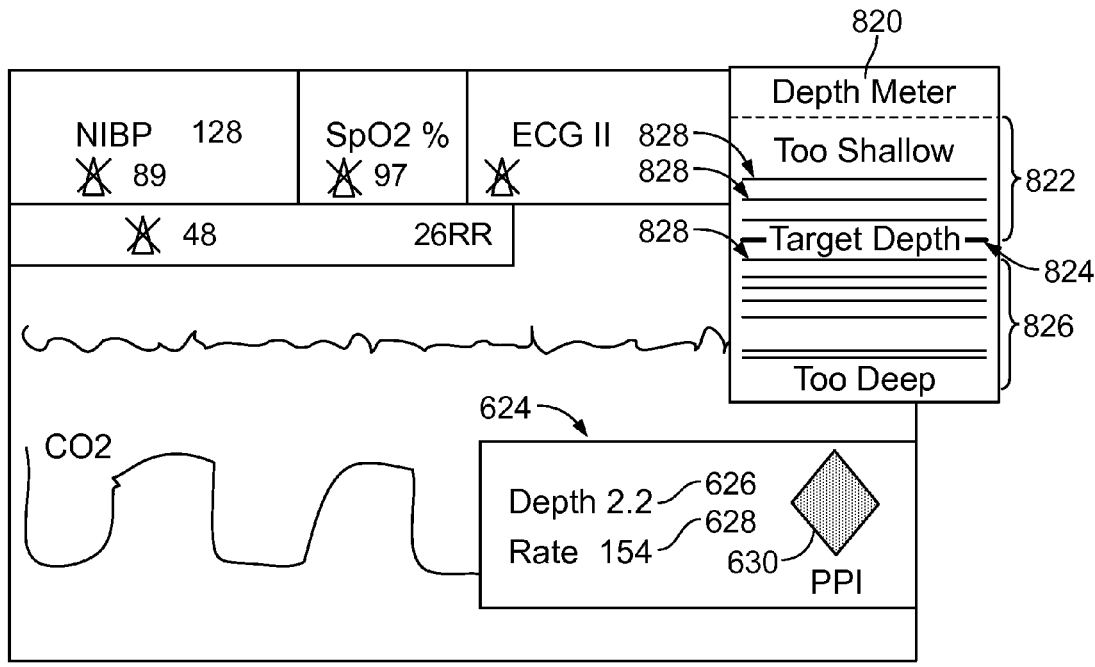
FIGS. 8A and 8B show screenshots with gradiated scales indicating target chest compression depths.

As shown in FIG. 8A, a visual representation of CPR quality can include an indicator of CPR compression depth such as a CPR depth meter 820. The CPR depth meter 820 can be automatically displayed upon detection of CPR chest compressions.

On the CPR depth meter 820, depth bars 828 visually indicate the depth of the administered CPR compressions relative to a target depth 824. As such, the relative location of the depth bars 828 in relation to the target depth 824 can serve as a guide to a rescuer for controlling the depth of CPR compressions. For example, depth bars 828 located in a region 822 above the target depth bar 824 indicate that the compressions were shallower than the target depth, and depth bars 828 located in a region 826 below the target depth bar 824 indicate that the compressions were deeper than the target depth. Again, then depth is inadequate (along with perhaps other factors) for a sufficient time to indicate that the rescuer is fatiguing, an indicator to switch rescuers may be provided in the manners discussed above.

Figure 8B:
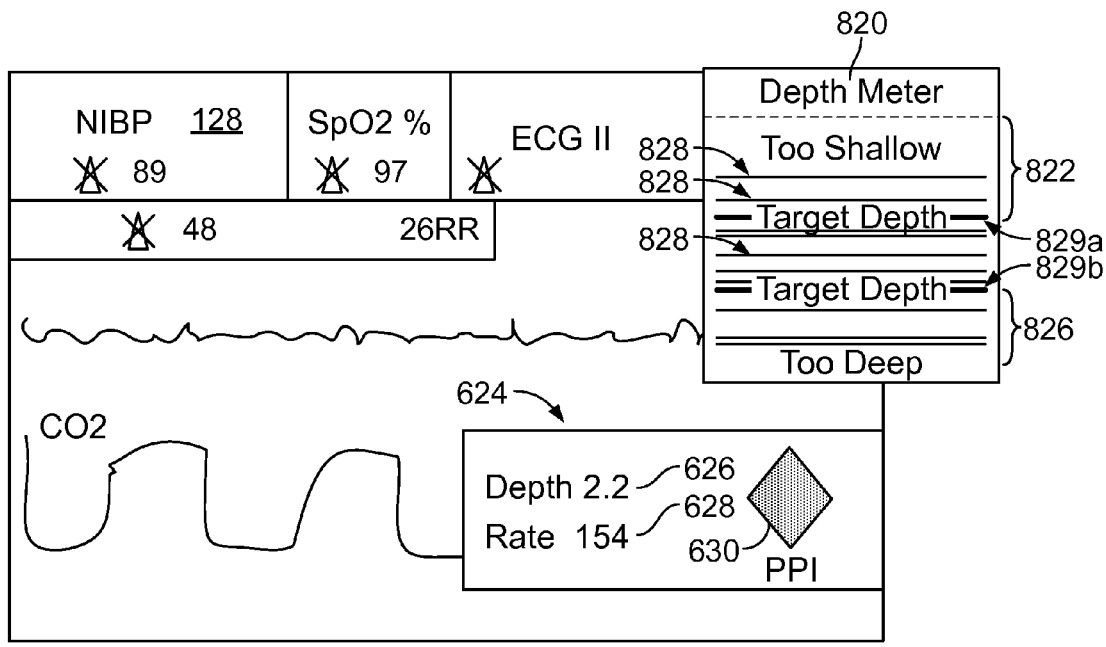

While the example shown in FIG. 8A displayed the target depth 824 as a single bar, in some additional examples, the target depth can be displayed as a range of preferred depths. For example, two bars 829a and 829b can be included on the depth meter 820 providing an acceptable range of compression depths (e.g., as shown in FIG. 8B). Additionally, in some examples, compressions that have depths outside of an acceptable range can be highlighted in a different color than compressions that have depths within the acceptable range of compression depths.

The depth bars 828 displayed on the CPR depth meter 820 can represent the compression depths of the most recent CPR compressions administered by the rescuer. For example, the CPR depth meter 820 can display depth bars 828 for the most recent 10-20 CPR compressions (e.g., the most recent 10 CPR compressions, the most recent 15 compressions, the most recent 20 CPR compressions). In another example, CPR depth meter 820 can display depth bars 828 for CPR compressions administered during a particular time interval (e.g., the previous 10 seconds, the previous 20 seconds).

In some additional embodiments, physiological information (e.g., physiological information such as end-tidal CO2 information, arterial pressure information, volumetric CO2, pulse oximetry (presence of amplitude of waveform possibly), and carotid blood flow (measured by Doppler) can be used to provide feedback on the effectiveness of the CPR delivered at a particular target depth. Based on the physiological information, the system can automatically determine a target CPR compression depth (e.g., calculate or look-up a new CPR compression target depth) and provide feedback to a rescuer to increase or decrease the depth of the CPR compressions. Thus, the system can provide both feedback related to how consistently a rescuer is administering CPR compressions at a target depth, and feedback related to whether the target depth should be adjusted based on measured physiological parameters. If the rescuers does not respond to such feedback and continues performed sub-optimal CPR, the system may then display an additional message to switch out the person performing CPR chest compressions.

In some examples, the system regularly monitors and adjusts the target CPR compression depth. In order to determine a desirable target depth, the system makes minor adjustments to the target CPR compression depth and observes how the change in compression depth affects the observed physiological parameters before determining whether to make further adjustments to the target compression depth. More particularly, the system can determine an adjustment in the target compression depth that is a fraction of an inch and prompt the rescuer to increase or decrease the compression depth by the determined amount. For example, the system can adjust the target compression depth by 0.1-0.25 inches (e.g., 0.1 inches to 0.15 inches, 0.15 to 0.25 inches, about 0.2 inches) and provide feedback to the rescuer about the observed compression depth based on the adjusted target compression depth. Then, over a set period of time, the system can observe the physiological parameters and, based on trends in the physiological parameters without making further adjustments to the target compression depth and at the end of the set time period, may determine whether to make further adjustments to the target compression depth.

And again, the actual performance of the rescuer against the revised target may be continually monitored to determine when the rescuer's performance has fallen below an acceptable level, so that the rescuer and perhaps others may be notified to change who is performing the chest compressions. Also, each of the relevant parameters of patient condition discussed above with respect to the various screenshots may be made one of multiple inputs to a process for determining when rescuers who are performing one component of a rescue technique should be switched out with another rescuer, such as for reasons of apparent fatigue on the part of the first rescuer.

While at least some of the embodiments described above describe techniques and displays used during manual human-delivered chest compressions, similar techniques and displays can be used with automated chest compression devices such as the AUTOPULSE device manufactured by ZOLL Medical, MA.

Figure 9:
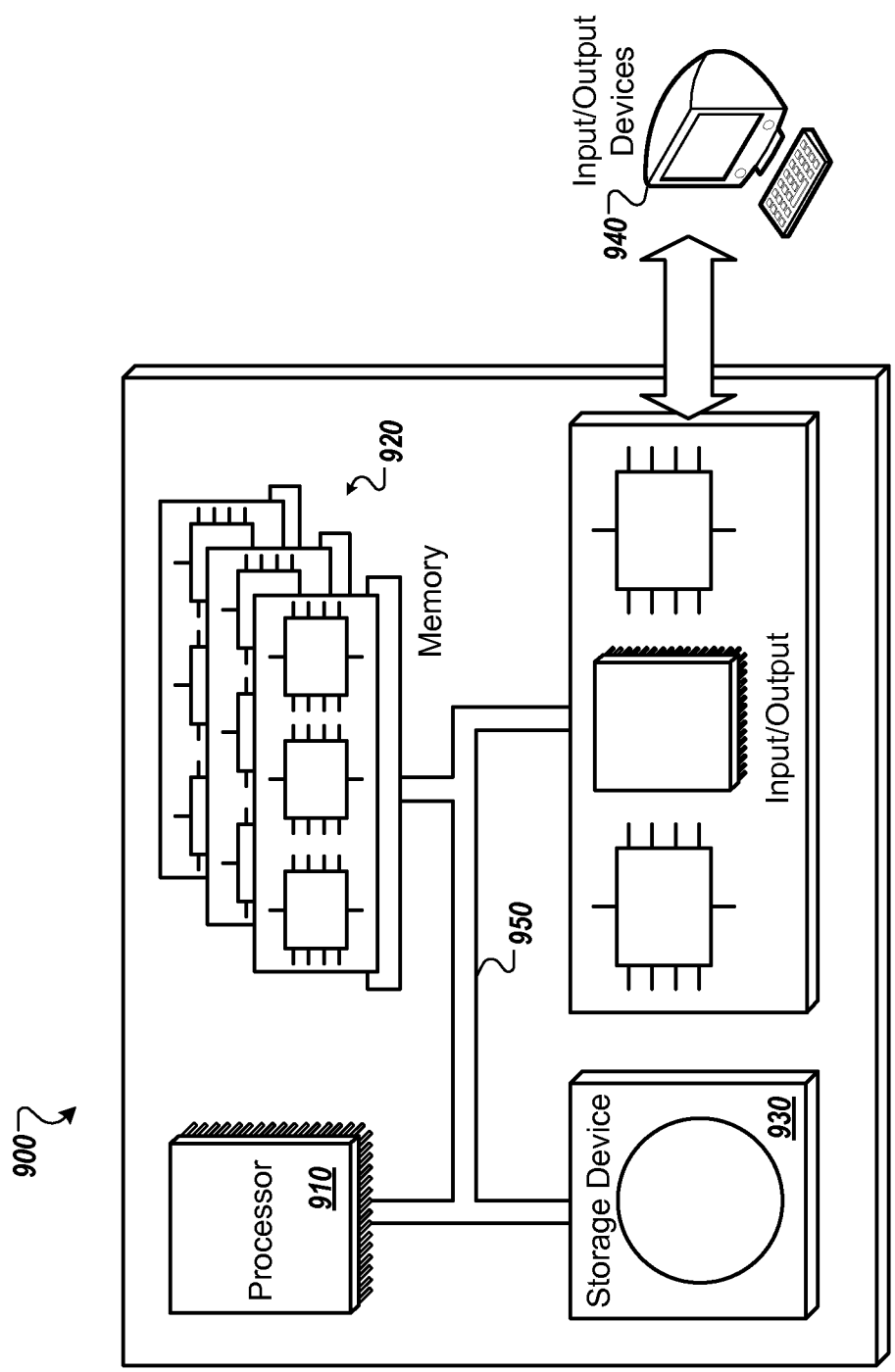
FIG. 9 shows a general computer system that can provide interactivity with a user of a medical device, such as feedback to a user in the performance of CPR.

The particular techniques described here may be assisted by the use of a computer-implemented medical device, such as a defibrillator that includes computing capability. Such defibrillator or other device is shown in FIG. 9, and may communicate with and/or incorporate a computer system 800 in performing the operations discussed above, including operations for computing the quality of one or more components of CPR provided to a victim and generating feedback to rescuers, including feedback to change rescuers who are performing certain components of the CPR. The system 900 may be implemented in various forms of digital computers, including computerized defibrillators laptops, personal digital assistants, tablets, and other appropriate computers. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 900 includes a processor 910, a memory 920, a storage device 930, and an input/output device 940. Each of the components 910, 920, 930, and 940 are interconnected using a system bus 950. The processor 910 is capable of processing instructions for execution within the system 900. The processor may be designed using any of a number of architectures. For example, the processor 910 may be a CISC (Complex Instruction Set Computers) processor, a RISC (Reduced Instruction Set Computer) processor, or a MISC (Minimal Instruction Set Computer) processor.

In one implementation, the processor 910 is a single-threaded processor. In another implementation, the processor 910 is a multi-threaded processor. The processor 910 is capable of processing instructions stored in the memory 920 or on the storage device 930 to display graphical information for a user interface on the input/output device 940.

The memory 920 stores information within the system 900. In one implementation, the memory 920 is a computer-readable medium. In one implementation, the memory 920 is a volatile memory unit. In another implementation, the memory 920 is a non-volatile memory unit.

The storage device 930 is capable of providing mass storage for the system 900. In one implementation, the storage device 930 is a computer-readable medium. In various different implementations, the storage device 930 may be a floppy disk device, a hard disk device, an optical disk device, or a tape device.

The input/output device 940 provides input/output operations for the system 900. In one implementation, the input/output device 940 includes a keyboard and/or pointing device. In another implementation, the input/output device 940 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having an LCD (liquid crystal display) or LED display for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Many other implementations other than those described may be employed, and may be encompassed by the following claims.

What is claimed is:

1. An external defibrillator system for managing care of a person receiving emergency cardiac assistance, the system comprising:
one or more capacitors for delivering a defibrillating shock to the person;
one or more electronic ports for receiving signals from sensors for obtaining indications of an electrocardiogram (ECG) for the person;
a patient treatment module executable on one or more computer processors to provide a determination of a metric indicative of a likelihood of success from delivering a future defibrillating shock to the person with the one or more capacitors, using (a) information about an indicator of success associated with a prior defibrillating shock, the indicator determined based on a segment of ECG waveform corresponding to a time period following application of the prior defibrillating shock, and (b) a value that is a function of current ECG signals from the person; and an output mechanism comprising a visual display that is configured to display one of multiple possible indications that each indicate a degree of the likelihood of success from delivering a defibrillating shock to the person with the one or more capacitors.

2. The system of claim 1, wherein the output mechanism comprises an interlock that prevents delivery of the defibrillating shock unless the likelihood of success exceeds a determined value.

3. The system of claim 1, wherein the patient treatment module comprises an ECG analyzer for generating an amplitude spectrum area (AMSA) value, and wherein the patient treatment module uses the information about the indicator of success associated with the prior defibrillating shock to adjust the AMSA value.

4. The system of claim 1, wherein the patient treatment module comprises an ECG analyzer for generating an indication of heart rate for the person.

5. The system of claim 1, wherein the patient treatment module comprises an ECG analyzer for generating an indication heart rate variability for the person.

6. The system of claim 1, wherein the patient treatment module comprises an ECG analyzer for generating an indication of ECG amplitude for the person.

7. The system of claim 6, wherein the indication of ECG amplitude comprises an RMS measurement, measured peak-to-peak, peak-to-trough, or an average of peak-to-peak or peak-to-trough over a specified interval.

8. The system of claim 1, wherein the patient treatment module comprises an ECG analyzer for generating an indication of a first derivative of ECG amplitude for the person.

9. The system of claim 1, wherein the patient treatment module comprises an ECG analyzer for generating an indication of a second derivative of ECG amplitude for the person.

10. The system of claim 1, where the patient treatment module is programmed to determine whether the prior defibrillating shock was at least partially successful, and based at least in part on the determination of whether the prior defibrillating was at least partially successful, modifying a calculation of the likelihood of success from delivering the future defibrillating shock.

11. The system of claim 1, wherein determining the likelihood of success from delivering a future defibrillating shock to the person depends on a determination of whether the prior defibrillating shock delivered to the person resulted in a predetermined heart rhythm within the segment of ECG waveform corresponding to the time period following the application of the prior defibrillating shock.

12. The system of claim 1, wherein determining the likelihood of success from delivering a future defibrillating shock comprises performing a mathematical transform on data representing the ECG.

13. The system of claim 12, wherein the mathematical transform is selected form a group consisting of Fourier, discrete Fourier, Hilbert, discrete Hilbert, wavelet, and discrete wavelet methods.

14. The system of claim 1, wherein determining the likelihood of success from delivering a future defibrillating shock comprises performing a calculation by an operation selected form a group consisting of logistic regression, table look-up, neural network, and fuzzy logic.

15. The system of claim 1, wherein the patient treatment module is programmed to determine the likelihood of success from delivering a future defibrillating shock using at least one patient-dependent physical parameter separate from a patient ECG reading.

16. The system of claim 1, wherein the patient treatment module is programmed to determine the likelihood of success from delivering a future defibrillating shock using at a measure of trans-thoracic impedance of the person.

17. A method for managing care of a person receiving emergency cardiac assistance, the method comprising:
monitoring, with an external defibrillator, electrocardiogram (ECG) data from the person receiving emergency cardiac assistance;
determining whether a prior defibrillating shock was administered;
determining a likelihood of future defibrillation shock success using (a) information about an indicator of success associated with the prior defibrillating shock, the indicator determined based on a segment of the ECG data corresponding to a time period following application of the prior defibrillating shock, and (b) a value that is a function of a portion of the ECG data representing current ECG signals from the person; and
affecting control of the external defibrillator based on the determination of whether a present defibrillation shock will likely be effective, affecting control of the defibrillator comprising electronically displaying, to a user, the value of multiple possible values in a range that indicates the likelihood of future defibrillation shock success.

18. The method of claim 17, wherein determining the likelihood of future defibrillation shock success comprises determining the value of the multiple possible values that is a function of electrocardiogram amplitude at particular different frequencies or frequency ranges.

19. The method of claim 18, wherein determining the value of multiple possible values comprises determining an amplitude spectrum area (AMSA) value for the ECG data.

20. The method of claim 19, wherein determining value of multiple possible values further comprises adjusting the determined AMSA value using the information about the indicator of success associated with the prior defibrillating shock.

21. The method of claim 20, further comprising determining whether the adjusted AMSA value exceeds a predetermined threshold value.

22. The method of claim 21, further comprising providing a visual, audible, or tactile alert that a shockable situation exists for the person, if the adjusted AMSA value is determined to exceed the predetermined threshold value.

23. The method of claim 17, further comprising determining whether the prior defibrillating shock was at least partially successful, and based at least in part on the determination of whether the prior defibrillating was at least partially successful, modifying a calculation of the likelihood of success from delivering the future defibrillating shock.

24. The method of claim 17, wherein determining the likelihood of success from delivering a future defibrillating shock comprises performing a mathematical transform on the ECG data.

25. The method of claim 24, wherein the mathematical transform is selected form a group consisting of Fourier, discrete Fourier, Hilbert, wavelet, and discrete wavelet methods.

26. The method of claim 25, wherein determining the likelihood of success from delivering a future defibrillating shock comprises performing a calculation by an operation selected form a group consisting of logistic regression, table look-up, neural network, and fuzzy logic.

27. The method of claim 17, where the likelihood of success from delivering a future defibrillating shock is determined using at least one patient-dependent physical parameter separate from a patient ECG reading.

28. The method of claim 27, wherein the physical parameter is trans-thoracic impedance of the person receiving emergency cardiac care.

29. The method of claim 28, wherein the indication of the trans-thoracic impedance is determined from signals sensed by a plurality of electrocardiogram leads that also provide the ECG data.

30. The method of claim 17, further comprising cyclically repeating the actions of monitoring, determining, identifying and providing the indication.

31. The method of claim 17, further comprising identifying compression depth of chest compressions performed on the person, using a device on the person's sternum and in communication with the external defibrillator, and providing feedback to a rescuer performing the chest compressions regarding rate of compression, depth of compression, or both.

32. The method of claim 17, wherein affecting control of the defibrillator comprises preventing a user from delivering the defibrillating shock unless the determination of whether the defibrillating shock will be effective exceeds a determined likelihood level.

33. The method of claim 17, wherein the likelihood of current shock success is determined or modified using a determination of a value of trans-thoracic impedance of the person.

* * * * *